(12) United States Patent
Gharib et al.

(10) Patent No.: US 8,989,866 B2
(45) Date of Patent: Mar. 24, 2015

(54) SYSTEM AND METHODS FOR ASSESSING THE NEUROMUSCULAR PATHWAY PRIOR TO NERVE TESTING

(71) Applicant: NuVasive, Inc., San Diego, CA (US)

(72) Inventors: James E. Gharib, San Diego, CA (US); Allen Farquhar, Portland, OR (US); Kelli Howell, San Diego, CA (US); Doug Layman, San Diego, CA (US); Albert Pothier, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 14/029,606

(22) Filed: Sep. 17, 2013

(65) Prior Publication Data

US 2014/0148796 A1    May 29, 2014

Related U.S. Application Data

(63) Continuation of application No. 11/665,038, filed as application No. PCT/US2005/036089 on Oct. 7, 2005, now Pat. No. 8,538,539.

(60) Provisional application No. 60/617,142, filed on Oct. 7, 2004, provisional application No. 60/622,494, filed on Oct. 26, 2004, provisional application No. 60/721,424, filed on Sep. 27, 2005.

(51) Int. Cl.
*A61N 1/00* (2006.01)
*A61B 19/00* (2006.01)
(Continued)

(52) U.S. Cl.
CPC .............. *A61B 19/46* (2013.01); *A61B 5/04001* (2013.01); *A61B 5/0488* (2013.01); *A61B 5/1106* (2013.01); *A61B 5/4836* (2013.01); *A61B 17/02* (2013.01); *A61B 17/17* (2013.01);
(Continued)

(58) Field of Classification Search
CPC .......................... A61N 1/36003; A61N 1/3605
USPC .................................................. 607/48, 2, 1
See application file for complete search history.

(56) References Cited

U.S. PATENT DOCUMENTS 2,736,002 A    2/1956 Oriel
3,785,368 A    1/1974 McCarthy et al.
(Continued)

FOREIGN PATENT DOCUMENTS

WO    WO 01/37728    5/2001
WO    WO 03/026482   4/2003
(Continued)

OTHER PUBLICATIONS

Ali, H. et al., "Quantitative Assessment of Residual Antidepolarizing Block (Part I)," Brit J Anaesth (1971) 43:473-477.
(Continued)

*Primary Examiner* — Christopher D Koharski
*Assistant Examiner* — Philip Edwards
(74) *Attorney, Agent, or Firm* — Jonathan Spangler; Heather Prado

(57) ABSTRACT

The present invention involves a system and methods for assessing the state of the neuromuscular pathway to ensure further nerve tests aimed at detecting at least one of a breach in a pedicle wall, nerve proximity, nerve direction, and nerve pathology, are not conducted when neuromuscular blockade levels may decrease the reliability of the results.

20 Claims, 44 Drawing Sheets

(51) Int. Cl.

| | | |
|---|---|---|
| *A61B 5/04* | (2006.01) | |
| *A61B 5/0488* | (2006.01) | |
| *A61B 5/11* | (2006.01) | |
| *A61B 5/00* | (2006.01) | |
| *A61B 17/02* | (2006.01) | |
| *A61B 17/17* | (2006.01) | |
| *A61B 17/88* | (2006.01) | |
| *A61N 1/04* | (2006.01) | |

(52) U.S. Cl.
CPC .......... *A61B 17/8875* (2013.01); *A61N 1/0456* (2013.01); *A61B 5/6823* (2013.01); *A61B 2505/05* (2013.01); *A61B 2562/046* (2013.01)
USPC ..................................... 607/48; 607/2; 607/1

(56) References Cited

U.S. PATENT DOCUMENTS

| | | |
|---|---|---|
| 4,291,705 A | 9/1981 | Severinghaus et al. |
| 4,545,374 A | 10/1985 | Jacobson |
| 4,962,766 A | 10/1990 | Herzon |
| 5,277,197 A | 1/1994 | Church et al. |
| 5,284,153 A | 2/1994 | Raymond et al. |
| 5,284,154 A | 2/1994 | Raymond et al. |
| 5,474,558 A | 12/1995 | Neubardt |
| 5,601,608 A | 2/1997 | Mouchawar |
| 5,775,331 A | 7/1998 | Raymond et al. |
| 5,779,642 A | 7/1998 | Nightengale |
| 5,806,522 A | 9/1998 | Katims |
| 5,810,747 A | 9/1998 | Brudny et al. |
| 5,830,151 A | 11/1998 | Hadzic et al. |
| 5,928,158 A | 7/1999 | Aristides |
| 5,935,131 A | 8/1999 | Bonutti |
| 6,011,985 A | 1/2000 | Athan |
| 6,027,456 A | 2/2000 | Feler et al. |
| 6,038,469 A | 3/2000 | Karlsson et al. |
| 6,104,957 A | 8/2000 | Alo et al. |
| 6,224,549 B1 | 5/2001 | Drongelen |
| 6,259,945 B1 | 7/2001 | Epstein et al. |
| 6,266,558 B1 | 7/2001 | Gozani et al. |
| 6,292,701 B1 | 9/2001 | Prass et al. |
| 6,306,100 B1 | 10/2001 | Prass |
| 6,334,068 B1 | 12/2001 | Hacker |
| 6,389,312 B1 | 5/2002 | Duckert |
| 6,393,325 B1 | 5/2002 | Mann et al. |
| 6,425,859 B1 | 7/2002 | Foley et al. |
| 6,451,015 B1 | 9/2002 | Rittman et al. |
| 6,466,817 B1 | 10/2002 | Kaula et al. |
| 6,500,128 B2 | 12/2002 | Marino |
| 6,564,078 B1 | 5/2003 | Marino et al. |
| 6,671,547 B2 | 12/2003 | Lyster et al. |
| 6,819,956 B2 | 11/2004 | DiLorenzo |
| 6,926,728 B2 | 8/2005 | Zucherman et al. |
| 7,089,059 B1 | 8/2006 | Pless |
| 7,207,949 B2 | 4/2007 | Miles et al. |
| 7,470,236 B1 | 12/2008 | Kelleher et al. |
| 7,522,953 B2 | 4/2009 | Kaula et al. |
| 7,657,308 B2 | 2/2010 | Miles et al. |
| 7,664,544 B2 | 2/2010 | Miles et al. |
| 7,905,840 B2 | 3/2011 | Pimenta et al. |
| 7,963,927 B2 | 6/2011 | Kelleher et al. |
| 8,068,912 B2 | 11/2011 | Kaula et al. |
| 2001/0039949 A1 | 11/2001 | Loubser |
| 2002/0007129 A1 | 1/2002 | Marino |
| 2002/0198572 A1 | 12/2002 | Weiner |
| 2003/0105503 A1 | 6/2003 | Marino |
| 2008/0064976 A1 | 3/2008 | Kelleher et al. |
| 2008/0064977 A1 | 3/2008 | Kelleher et al. |
| 2008/0167574 A1 | 7/2008 | Farquhar et al. |
| 2009/0018610 A1 | 1/2009 | Gharib et al. |
| 2009/0177112 A1 | 7/2009 | Gharib et al. |

FOREIGN PATENT DOCUMENTS

| | | |
|---|---|---|
| WO | WO 03037170 A2 * | 5/2003 |
| WO | WO 03/037170 | 11/2003 |

OTHER PUBLICATIONS

Ali, H. et al., "Stimulus Frequency in the Detection of Neuromuscular Block in Humans," Brit J Anaesth (1970) 42:967-978.

Engbaek J. et al., "Monitoring of neuromuscular transmission by electromyography (II). Evoked compound EMG area, amplitude and duration compared to mechanical twitch recording during onset and recovery of pancuronium-induced blockade in the cat", Acta Anaesthesiologica Scandinavica (1993) 37(3):788-798.

Ghai, B., et al., "Neuromuscular Monitoring: A Review," J Anaesth Clin Pharmacol (2006) 22(4):347-356.

International Search Report in corresponding International Application No. PCT/US05/36089 mailed Jun. 1, 2006.

Kitajima, T. et al., "Differential effects of vecuronium on the thumb and the big toe muscles evaluated by acceleration measurement," J Anesth (1994) 8:143-145.

Leslie, K. et al., "Common Peroneal Nerve Stimulation for Neuromuscular Monitoring: Evaluation in Awake Volunteer and Anesthetized Patients," Anest Analg (1999) 88:197-203.

Minahan R., et al., "The Effect of Neuromuscular Blockade on Pedicle Screw Stimulation Thresholds," Spine (2000) 25(19):2526-2530.

\* cited by examiner

NeuroVision JJB® Summary Test Report

| Control Unit Serial Number | Procedure Date: September 24, 2005 |
|---|---|
|  | Report Period: 10:30 – 11:24 |

To be completed by Surgeon / OR staff          (use patient label if available)

Physician_____     Procedure_____

Patient ID / Medical Record #_____

Procedure Data

Stimulated EMG – Stop on First Response

| Time | Channel/Myotome | Side | Level | Tested | Threshold (mA) |
|---|---|---|---|---|---|
| 11:18:52 | all | Right | L5 | Screw | >20 |
| 11:18:58 | all | Right | L4 | Screw | >20 |
| 11:19:06 | 3 BF Right | Left | L5 | Screw | 17 |
| 11:19:14 | 3 BF Right | Left | L4 | Screw | 19 |

Dynamic EMG

| Time | Channel/Myotome | Side | Level | Tested | Threshold (mA) | Color |
|---|---|---|---|---|---|---|
| 11:17:53 | all | Right | L5 | Pilot Hole | >20 | green |
| 11:18:07 | all | Right | L4 | Pilot Hole | >20 | green |
| 11:18:07 | 3 BF Right | Right | L4 | Pilot Hole | 20 | green |
| 11:18:07 | all | Right | L4 | Pilot Hole | >20 | green |
| 11:18:07 | 3 BF Right | Right | L4 | Pilot Hole | 20 | green |
| 11:18:22 | 3 BF Right | Left | L5 | Pilot Hole | 14 | green |
| 11:18:22 | all | Left | L5 | Pilot Hole | >20 | green |
| 11:18:22 | 3 BF Right | Left | L5 | Pilot Hole | 20 | green |
| 11:18:22 | all | Left | L5 | Pilot Hole | >20 | green |
| 11:18:22 | 3 BF Right | Left | L5 | Pilot Hole | 17 | green |
| 11:18:38 | all | Left | L4 | Pilot Hole | >20 | green |

FIG. 35A

| Nerve Detection EMG | | | | | |
|---|---|---|---|---|---|
| Time | Channel/Myotome | Side | Level | Threshold (mA) | Color |
| 10:34:03 | 1 VM Left | Left | N/A | 11 | green |
| 10:34:03 | all | Left | N/A | >20 | green |
| 10:34:03 | 2 TA Right | Left | N/A | 20 | green |
| 10:34:03 | all | Left | N/A | >20 | green |
| 10:34:03 | 3 BF Right | Left | N/A | 15 | green |
| 10:34:03 | 3 BF Right | Left | N/A | 8 | yellow |
| 10:34:03 | 3 BF Left | Left | N/A | 16 | green |
| 11:16:03 | all | Right | L4-L5 | >20 | green |
| 11:16:03 | 3 BF Right | Right | L4-L5 | 20 | green |
| 11:16:03 | all | Right | L4-L5 | >20 | green |
| 11:16:03 | 3 BF Right | Right | L4-L5 | 19 | green |
| 11:16:03 | 3 BF Right | Right | L4-L5 | 5 | yellow |
| 11:16:03 | 3 BF Right | Right | L4-L5 | 12 | green |
| 11:16:03 | all | Right | L4-L5 | >20 | green |
| 11:16:03 | 3 BF Right | Right | L4-L5 | 12 | green |
| 11:16:51 | 3 BF Right | Right | L4-L5 | 16 | green |

| Twitch Test | | |
|---|---|---|
| Time | Channel/Myotome | Ratio |
| 10:31:29 | 1 VM Left | >99% |
| 10:35:35 | 3 BF Left | >99% |

| Free Run EMG (number of events) | | | | | | | |
|---|---|---|---|---|---|---|---|
| L.VM | L.TA | L.BF | L.GM | R.VM | R.TA | R.BF | R.GM |
| 1 | 1 | 1 | 1 | | | 4 | 5 |

Total Free Run Time: 41 Minutes
Monitoring time without events at end of case: 0 Minutes

FIG. 35B

Surgeon Operative Notes

Signature        Date

FIG. 35C

```
                          Time 10:31:29
┌Twitch Test──────────────────────────────────────────────────────┐
│    Left 1 VM           Direct Stim        13 mA      >99%       │
└─────────────────────────────────────────────────────────────────┘

Time 10:33:36
┌Free Run EMG    (Vpp readings in microvolts)────────────────────┐
│  Time     L.VM  L.TA  L.BF  L.GM  R.VM  R.TA  R.BF  R.GM Sensitivity│
│10:32:18                      56                      53    50   │
│10:33:36  End                                                    │
└─────────────────────────────────────────────────────────────────┘

Time 10:34:03
┌Nerve Detection EMG Threshold in milliamps──────────────────────┐
│        Stimulation Site:   Left                                 │
│      Time           Myotome         Threshold       Color       │
│    10:34:06       Left 1 VM           11 mA         green       │
│    10:34:12                          >20 mA         green       │
│    10:34:13       Right 2 TA          20 mA         green       │
│    10:34:13                          >20 mA         green       │
│    10:34:18       Right 3 BF          15 mA         green       │
│    10:34:20       Right 3 BF           8 mA         yellow      │
│    10:34:22       Left 3 BF           16 mA         green       │
│    10:34:27    Detection End                                    │
└─────────────────────────────────────────────────────────────────┘

Time 10:35:35
┌Twitch Test──────────────────────────────────────────────────────┐
│    Left 3 BF           Direct Stim        19 mA      >99%       │
└─────────────────────────────────────────────────────────────────┘
```

FIG. 36B

Time 11:15:48

Free Run EMG (Vpp readings in microvolts)

| Time | L.VM | L.TA | L.BF | L.GM | R.VM | R.TA | R.BF | R.GM | Sensitivity |
|---|---|---|---|---|---|---|---|---|---|
| 10:36:10 | | | | | | | 412 | | 50 |
| 10:36:11 | | | | | | | 688 | | 50 |
| 10:36:19 | | | | | | | 268 | | 50 |
| 10:36:19 | | | | | | | | 72 | 50 |
| 10:36:19 | | | | | | | | 988 | 50 |
| 10:36:35 | | | | | | 68 | | | 50 |
| 10:36:35 | | | | | | | 584 | | 50 |
| 10:36:36 | | | | | | | 780 | | 50 |
| 11:10:54 | 56 | | 60 | 108 | | | | | 50 |
| 11:15:49 End | | | | | | | | | |

Time 11:16:03

Nerve Detection EMG Threshold in milliamps
Stimulation Site: Right L4-L5 Dilator

| Time | Myotome | Threshold | Color |
|---|---|---|---|
| 11:16:05 | | >20 mA | green |
| 11:16:05 | Right 3 BF | 20 mA | green |
| 11:16:06 | | >20 mA | green |
| 11:16:12 | Right 3 BF | 19 mA | green |
| 11:16:17 | Right 3 BF | 5 mA | yellow |
| 11:16:21 | Right 3 BF | 12 mA | green |
| 11:16:22 | | >20 mA | green |
| 11:16:25 | Right 3 BF | 12 mA | green |
| 11:16:29 | Detection End | | |

Time 11:16:51

Nerve Detection EMG Threshold in milliamps
Stimulation Site: Right L4-L5 Probe

| Time | Myotome | Threshold | Color |
|---|---|---|---|
| 11:16:54 | Right 3 BF | 16 mA | green |
| 11:17:00 | Detection End | | |

Time 11:17:39

Free Run EMG (Vpp readings in microvolts)

| Time | L.VM | L.TA | L.BF | L.GM | R.VM | R.TA | R.BF | R.GM | Sensitivity |
|---|---|---|---|---|---|---|---|---|---|
| 11:17:39 End | | | | | | | | | |

FIG. 36C

Time 11:17:53

Dynamic EMG Threshold in milliamps
Stimulation Site: Right L5 Pilot Hole

| Left | Myotome | Threshold | Color |
|---|---|---|---|
| 11:17:55 | | >20 mA | green |
| 11:17:59 | Dynamic End | | |

Time 11:18:07

Dynamic EMG Threshold in milliamps
Stimulation Site: Right L4 Pilot Hole

| Left | Myotome | Threshold | Color |
|---|---|---|---|
| 11:18:09 | | >20 mA | green |
| 11:18:09 | Right 3 BF | 20 mA | green |
| 11:18:09 | | >20 mA | green |
| 11:18:10 | Right 3 BF | 20 mA | green |
| 11:18:13 | Dynamic End | | |

Time 11:18:22

Dynamic EMG Threshold in milliamps
Stimulation Site: Left L5 Pilot Hole

| Left | Myotome | Threshold | Color |
|---|---|---|---|
| 11:18:25 | Right 3 BF | 14 mA | green |
| 11:18:29 | | >20 mA | green |
| 11:18:28 | Right 3 BF | 20 mA | green |
| 11:18:28 | | >20 mA | green |
| 11:18:30 | Right 3 BF | 17 mA | green |
| 11:18:31 | Dynamic End | | |

Time 11:18:38

Dynamic EMG Threshold in milliamps
Stimulation Site: Left L4 Pilot Hole

| Left | Myotome | Threshold | Color |
|---|---|---|---|
| 11:18:40 | | >20 mA | green |
| 11:18:42 | Dynamic End | | |

FIG. 36D

Time 11:18:52
Stimulated EMG Threshold in milliamps – Stop on First Response
Stimulation Site: Right L5 Screw

| Left | Threshold | Right | Threshold |
|---|---|---|---|
| 1 VM | >20 | 1 VM | >20 |
| 2 TA | >20 | 2 TA | >20 |
| 3 BF | >20 | 3 BF | >20 |
| 4 GM | >20 | 4 GM | >20 |

Time 11:18:58
Stimulated EMG Threshold in milliamps – Stop on First Response
Stimulation Site: Right L4 Screw

| Left | Threshold | Right | Threshold |
|---|---|---|---|
| 1 VM | >20 | 1 VM | >20 |
| 2 TA | >20 | 2 TA | >20 |
| 3 BF | >20 | 3 BF | >20 |
| 4 GM | >20 | 4 GM | >20 |

Time 11:19:06
Stimulated EMG Threshold in milliamps – Stop on First Response
Stimulation Site: Left L5 Screw

| Left | Threshold | Right | Threshold |
|---|---|---|---|
| 1 VM | >20 | 1 VM | >20 |
| 2 TA | >20 | 2 TA | >20 |
| 3 BF | >20 | 3 BF | 17 |
| 4 GM | >20 | 4 GM | >20 |

Time 11:19:14
Stimulated EMG Threshold in milliamps – Stop on First Response
Stimulation Site: Left L4 Screw

| Left | Threshold | Right | Threshold |
|---|---|---|---|
| 1 VM | >20 | 1 VM | >20 |
| 2 TA | >20 | 2 TA | >20 |
| 3 BF | >20 | 3 BF | 19 |
| 4 GM | >20 | 4 GM | >20 |

FIG. 36E

SYSTEM AND METHODS FOR ASSESSING THE NEUROMUSCULAR PATHWAY PRIOR TO NERVE TESTING

CROSS REFERENCE TO RELATED APPLICATIONS

This application is a continuation of U.S. patent application Ser. No. 11/665,038 filed Apr. 9, 2007 (now issued as U.S. Pat. No. 8,538,539), which was the national state entry of PCT/US05/36089, filed on Oct. 7, 2005, which claims priority to U.S. Provisional Patent Application Ser. No. 60/617,142 filed on Oct. 7, 2004, U.S. Provisional Patent Application Ser. No. 60/622,494 filed on Oct. 26, 2004, and U.S. Provisional Patent Application Ser. No. 60/721,424 filed on Sep. 27, 2005, the entire contents of which are hereby expressly incorporated by reference into this disclosure as if set forth in their entirety herein.

BACKGROUND OF THE INVENTION

I. Field of the Invention

The present invention relates generally to a system and methods aimed at surgery, and more particularly to system and methods for testing the neuromuscular blockade level in a patient prior to conducting nerve tests aimed at detecting pedicle breaches, nerve proximity, nerve direction, and nerve pathology.

II. Discussion of the Prior Art

Despite ongoing advances in surgical methods, neurological impairment remains a serious concern during various surgical spine procedures. The misplacement of a pedicle screw or inadvertent contact between a surgical instrument and nerve during surgery may result in undesirable consequences, including pain, necessitation of revision surgeries, nerve damage, and a possible loss of muscle function. To avert such consequences, surgeons are increasingly relying on systems and methods that capitalize on the knowledge that electrically stimulating a nerve should result in detectable muscle activity.

While these existing EMG systems are significant advancements within the art, proliferated use of neuromuscular blocking agents (muscle relaxants) during surgery present certain challenges with the use of these systems. More specifically, surgeons must wait for a period of time to allow the neuromuscular blocking agents (NMBA) to wear off before initiating a nerve test, which increases surgery time and overall cost. NMBAs generally inhibit the neuromuscular pathway by binding to acetylcholine receptors on the postsynaptic membrane and hence, decrease neuromuscular transmission (transfer of a motor nerve impulse into the muscle) relative to the number of receptors occupied at a given time. This inhibition of the neuromuscular pathway is commonly referred to as neuromuscular block or blockade (NMB). If the neuromuscular pathway is sufficiently blocked, stimulation of a nerve will not result in the otherwise expected contraction of the corresponding muscle. NMB is a necessity during many surgical procedures in order to maintain a certain level of muscle relaxation, however, as mentioned it requires the surgeon to wait for the NMB to wear off prior to initiating a nerve test. If the nerve test is conducted too soon the muscle may fail to contract upon stimulation of the nerve and the stimulation current level at which the nerve is stimulated will appear to be higher than it truly is. This may create, in effect, a false positive wherein the surgeon may believe, for example, a pedicle wall has not been breached or a nerve farther from an instrument than it really is because of the erroneously high stimulation level detected.

The amount and metabolic rate of NMBA may vary from procedure to procedure and person to person. In addition, the present systems retain their effectiveness up to a certain level of NMB. Together this makes it difficult to determine when precisely nerve testing functions regain their effectiveness and surgeons must wait longer than necessary to ensure accurate results, which results in additional surgical time and increased costs. Being able to assess the neuromuscular pathway prior to initiating nerve testing would reduce the amount of waiting time needed and would thus represent a savings in time and costs to both the surgeon and patient.

Neuromuscular pathway testing is currently performed by specialists (neurophysiologists) trained in assessing the neurophysiologic information graphically represented on traditional EMG systems. While these individuals are oftentimes exceptionally skilled and highly trained, there exists the potential for human error on their part in reading and/or monitoring such traditional EMG systems. Moreover, the need for the neurophysiologist to assist in a surgical case adds complexity and challenges in scheduling surgical procedures, in that the schedules of both individuals need to coincide for them to work together. This may disadvantageously cause a patient to wait, while experiencing pain and/or other issues, for the scheduling conflicts of the surgeon and neurophysiologist to resolve. Because the neurophysiologist performs the actual neuromuscular pathway testing, there exists the potential for communication gaps to occur between the surgeon and the neurophysiologist such that the neuromuscular testing may not be conducted as desired by the surgeon. Also, with the attendant activity in the operating room (as well as other operating rooms where the neurophysiologist may be working), the possibility exists that the neuromuscular pathway testing may not be conducted in the desired manner based on inattentiveness of the neurophysiologist.

Based on the foregoing, a need exists for improved systems and methods for surgeon-directed nerve testing during surgery, and in particular a need exits for improved systems and methods for combining neuromuscular pathway assessment and nerve testing capabilities, all being performed by the surgeon. The present invention is directed towards fulfilling these needs.

SUMMARY OF THE INVENTION

The present invention includes a system and related methods for assessing the state of the neuromuscular pathway prior to and in combination with performing nerve testing functions aimed at detecting pedicle breaches during screw implantation, nerve proximity to surgical instruments employed in accessing a surgical target site, and nerve pathology monitoring. Advantageously, the system and methods of the present invention are surgeon-directed, meaning the surgeon is capable of directing all such functionality without the need for a neurophysiologist.

According to a broad aspect, the present invention involves a surgeon-directed surgical system, comprising a control unit, a surgical instrument, and peripheral nerve stimulation electrodes. The control unit has at least one of computer programming software, firmware and hardware capable of delivering a stimulation signal, receiving and processing neuromuscular responses due to the stimulation signal, and identifying a relationship between the neuromuscular response and the stimulation signal. The surgical instrument has at least one stimulation electrode electrically coupled to the control unit for transmitting a stimulation signal within a surgical corridor. Peripheral nerve stimulation electrodes are also coupled to the control unit for transmitting a stimulation signal to peripheral nerves outside a surgical corridor. The control unit is capable of determining the neuromuscular blockade level and at least one of pedicle integrity, nerve proximity, nerve direction, and nerve pathology based on the identified relationship between a stimulation signal and a corresponding neuromuscular response.

In a further embodiment of the surgical system of the present invention, the control unit is further equipped to communicate at least one of alpha-numeric and graphical information to a user regarding neuromuscular pathway status, and at least one of pedicle integrity, nerve proximity, nerve direction, and nerve pathology.

In a further embodiment of the surgical system of the present invention, the surgical instrument may comprise at least one of a device for testing screw placement integrity, a device for accessing a surgical target site, and a device for maintaining contact with a nerve during surgery.

In a further embodiment of the surgical system of the present invention, the surgical instrument comprises a screw test probe and wherein the control unit determines the degree of electrical communication between the screw test probe and an exiting spinal nerve root to assess whether a pedicle has been breached by at least one of hole formation and screw placement In a further embodiment of the surgical system of the present invention, the surgical instrument comprises a nerve root retractor and wherein the control unit determines nerve pathology based on the identified relationship between the neuromuscular response and the stimulation signal.

In a further embodiment of the surgical system of the present invention, the surgical instrument comprises a dilating instrument and wherein the control unit determines the proximity and direction between a nerve and the instrument based on the identified relationship between the neuromuscular response and the stimulation signal.

In a further embodiment of the surgical system of the present invention, the dilating instrument comprises at least one of a K-wire, an obturator, a dilating cannula, and a working cannula.

In a further embodiment of the surgical system of the present invention, the surgical instrument comprises a tissue retractor assembly and wherein the control unit determines the proximity between a nerve and the instrument based on the identified relationship between the neuromuscular response and the stimulation signal.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 35A-35C is an exemplary representation of a summary report according to one embodiment of the present invention; and FIGS. 36A-36E is an exemplary representation of a full report according to one embodiment of the present invention.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

Figure 1:
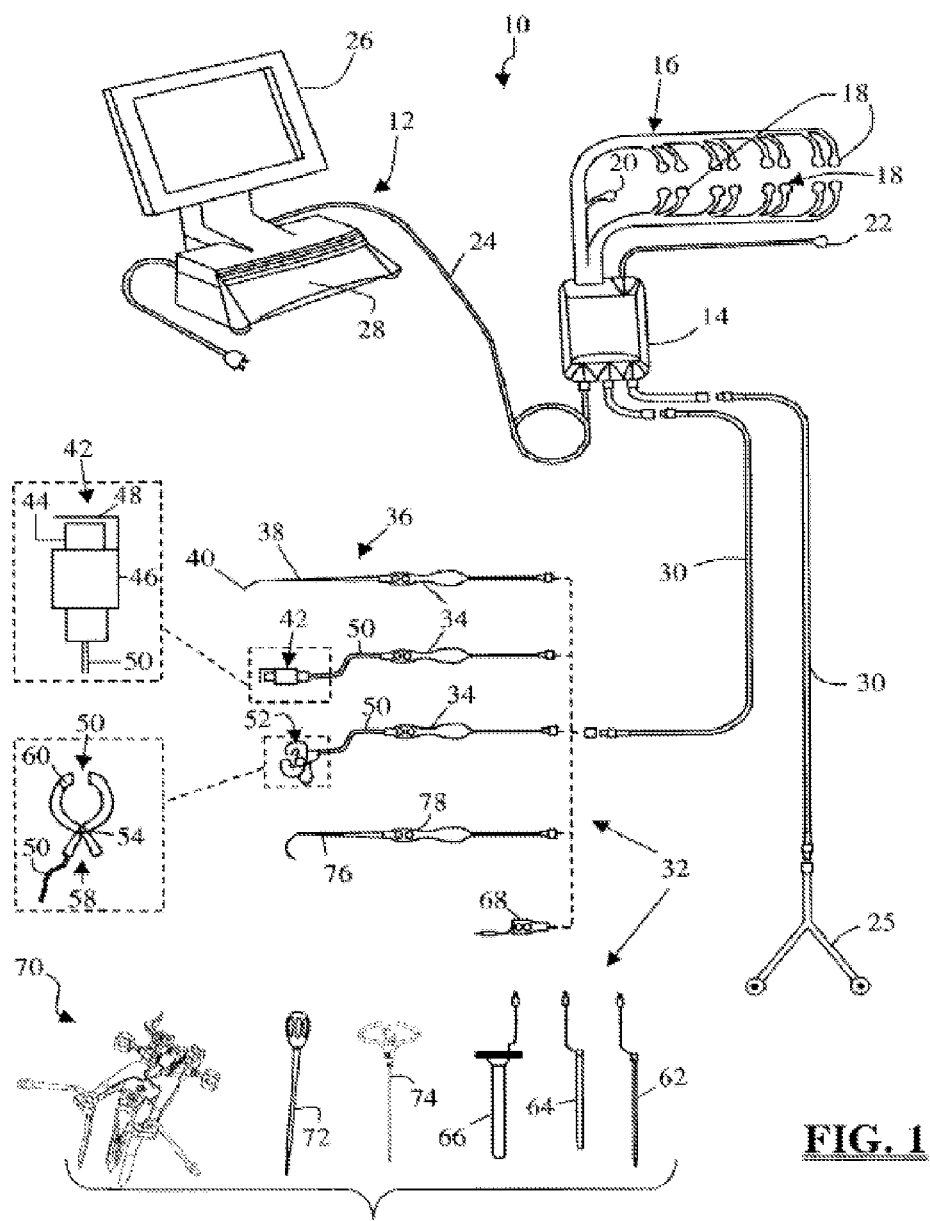
FIG. 1 is a perspective view of an exemplary surgeon-directed surgical system 10 capable of assessing the state of the neuromuscular pathway and nerve testing functions aimed at detecting pedicle breaches, nerve proximity (detection), and nerve pathology.

The present invention involves a surgeon-directed system and methods for assessing the neuromuscular pathway prior to and in combination with nerve testing procedures during surgery, including but not limited to pedicle integrity assessments (screw test), nerve proximity assessments (direction), and nerve pathology assessments (nerve root retraction). FIG. 1 illustrates, by way of example only, a surgeon-directed surgical system 10 capable of assessing the status of the neuromuscular pathway during a surgical procedure targeted to one of the lumbar, thoracic, or cervical regions of the spine, where nerve monitoring may be advantageous. The surgical system 10 is further capable of carrying out nerve testing functions including, but not necessarily limited to, pedicle screw testing, nerve proximity testing and nerve pathology monitoring. It is expressly noted that, although described herein largely in terms of use in spinal surgery, the surgeon-directed surgical system 10 and related methods of the present invention are suitable for use in any number of additional surgical procedures where neurological impairment is a concern.

The surgeon-directed surgical system 10 includes a control unit 12, a patient module 14, an EMG harness 16 (including eight pairs of EMG electrodes 18 and a return electrode 22 coupled to the patient module 14), and a host of various surgical accessories 32 capable of being coupled to the patient module 14 via one or more accessory cables 30 and/or coupling devices 42. The surgical accessories 32 may include, but are not necessarily limited to, devices for performing pedicle screw tests (such as a screw test probe 36), neural pathology monitoring devices (such as a nerve root retractor 76), coupling devices for electronically coupling surgical instruments to the system 10 (such as electric coupling devices 42,52 and stimulator driver 68), access components (such as a K-wire 62, one or more dilating cannula 64, a working cannula 66, and a tissue retraction assembly 70), and pilot hole forming components (such as a tap member 72, pedicle access probe 74, or other similar device), and devices for delivering peripheral stimulation signals (such as a pair—one positive and one negative—of peripheral nerve stimulation (PNS) electrodes 25).

Figure 2:
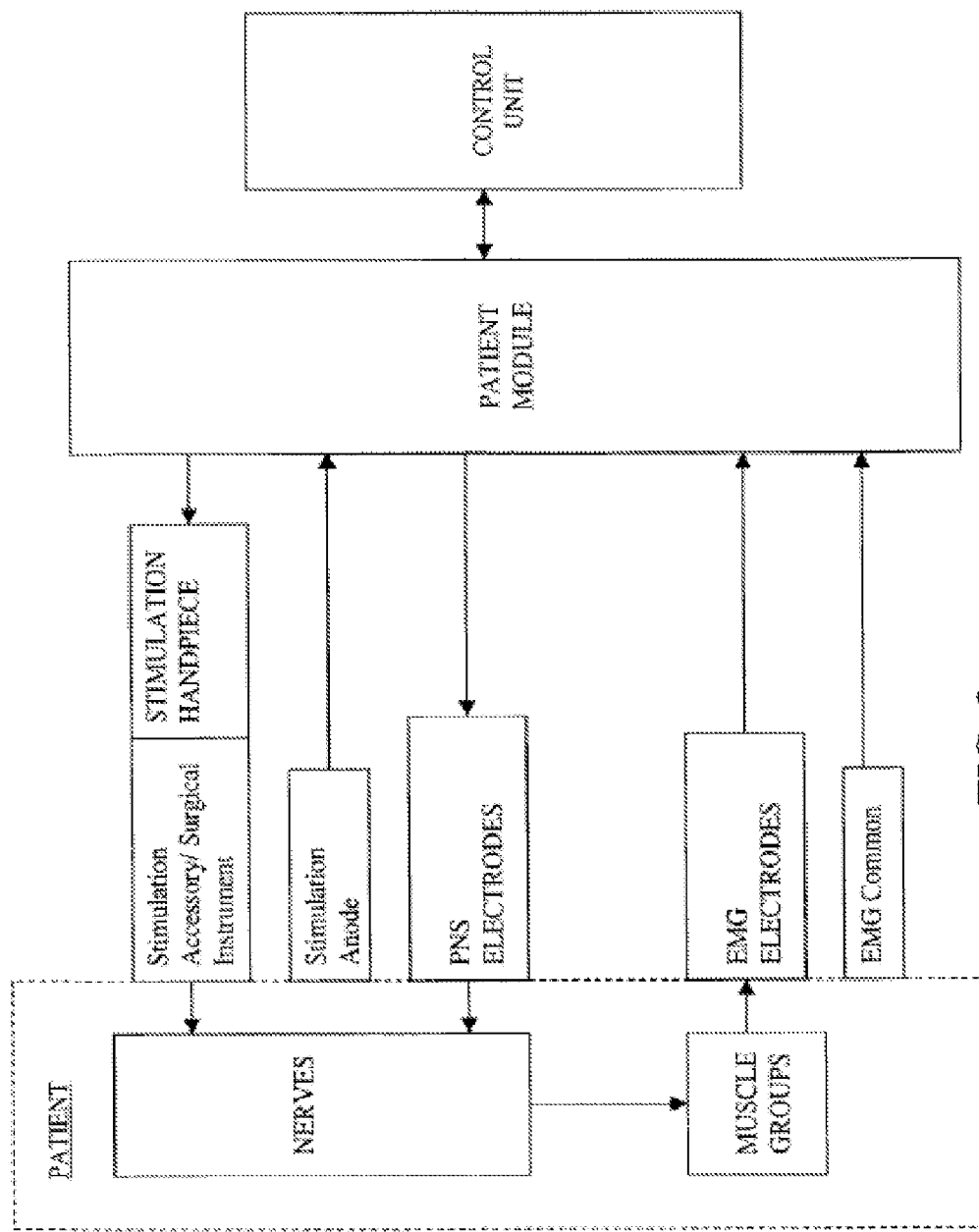
FIG. 2 is a block diagram of the surgical system 10 shown in FIG. 1.

A block diagram of the surgical system 10 is shown in FIG. 2, the operation of which is readily apparent in view of the following description. The control unit 12 includes a touch screen display 26 and a base 28, which collectively contain the essential processing capabilities for controlling the surgical system 10, preferably under the direction of a surgeon. The touch screen display 26 is preferably equipped with a graphical user interface (GUI) capable of communicating information to the surgeon and receiving instructions from the surgeon. The base 28 contains computer hardware and software that commands the stimulation sources, receives digitized signals and other information from the patient module 14, processes the EMG responses, and displays the processed data to the surgeon via the display 26. The primary functions of the software within the control unit 12 include receiving commands from the surgeon via the touch screen display 26, activating stimulation in the requested mode (including "Twitch Test" (neuromuscular pathway assessment), "Basic Screw Test" and/or "Dynamic Screw Test" (pedicle integrity assessment), "Detection" (nerve proximity), and "Nerve Retractor" (nerve pathology)), processing signal data according to defined algorithms (described below), displaying received parameters and processed data, and monitoring system status.

The patient module 14 is connected via a data cable 28 to the control unit 12, and contains the electrical connections to all electrodes, signal conditioning circuitry, stimulator drive and steering circuitry, and a digital communications interface to the control unit 12. In use, the control unit 12 is situated outside but close to the surgical field (such as on a cart adjacent the operating table) such that the display 26 is directed towards the surgeon for easy visualization. The patient module 14 should be located between the patient's legs or affixed to the end of the operating table at mid-leg level using a bedrail clamp. The position selected should be such that the EMG electrodes 18 can reach their farthest desired location without tension during the surgical procedure.

In a significant aspect of the present invention, the information displayed to the surgeon on the display 26 may include, but is not necessarily limited to, alpha-numeric and/or graphical information regarding NMP status, screw testing, nerve proximity, nerve pathology, myotome/EMG levels, stimulation levels, advance or hold instructions, and the instrument in use. In one embodiment (set forth by way of example only) the display includes the following components as set forth in Table 1:

TABLE 1

| Screen Component | Description |
|---|---|
| Spine Image 100 | An image of the human body/skeleton showing the electrode placement on the body, with labeled channel number tabs on each side (1-4 on the left and right). Left and right labels will show the patient orientation. The channel number tabs may be highlighted or colored depending on the specific function being performed. |
| Myotome & Level Names 102 | A label to indicate the Myotome name and corresponding Spinal Level(s) associated with the channel of interest. |
| Menu 104 | A drop down navigation component for toggling between functions. |
| Display Area 106 | Shows procedure-specific information including stimulation results 120. |
| Color Indication 108 | Enhances stimulation results with a color display of green, yellow, or red corresponding to the relative safety level determined by the system. In one embodiment, "Advance" or "Hold" instructions may be optionally displayed also corresponding to the relative safety level determined by the system in the Detection mode. |
| Function Indicator 110 | Graphics and/or name to indicate the currently active function (Twitch Test, Basic Screw Test, Dynamic Screw Test, Difference Screw Test, Detection, Nerve Retractor). In an alternate embodiment, Graphics and/or name may also be displayed to indicate the instrument in use, such as the dialator, K-wire, retractor blades, screw test instruments, and associated size information (if applicable) of the dialator, with the numeric size. If no instrument is in use, then no indicator is displayed. |
| Stimulation Bar 112 | A graphical stimulation indicator depicting the present stimulation status (e.g. on/off and stimulation current level) |
| Sequence Bar 114 | Shows the last seven stimulation results and provides for annotation of results. |
| EMG waveforms 116 | EMG waveforms may be optionally displayed on screen along with the stimulation results. |

Figure 3:
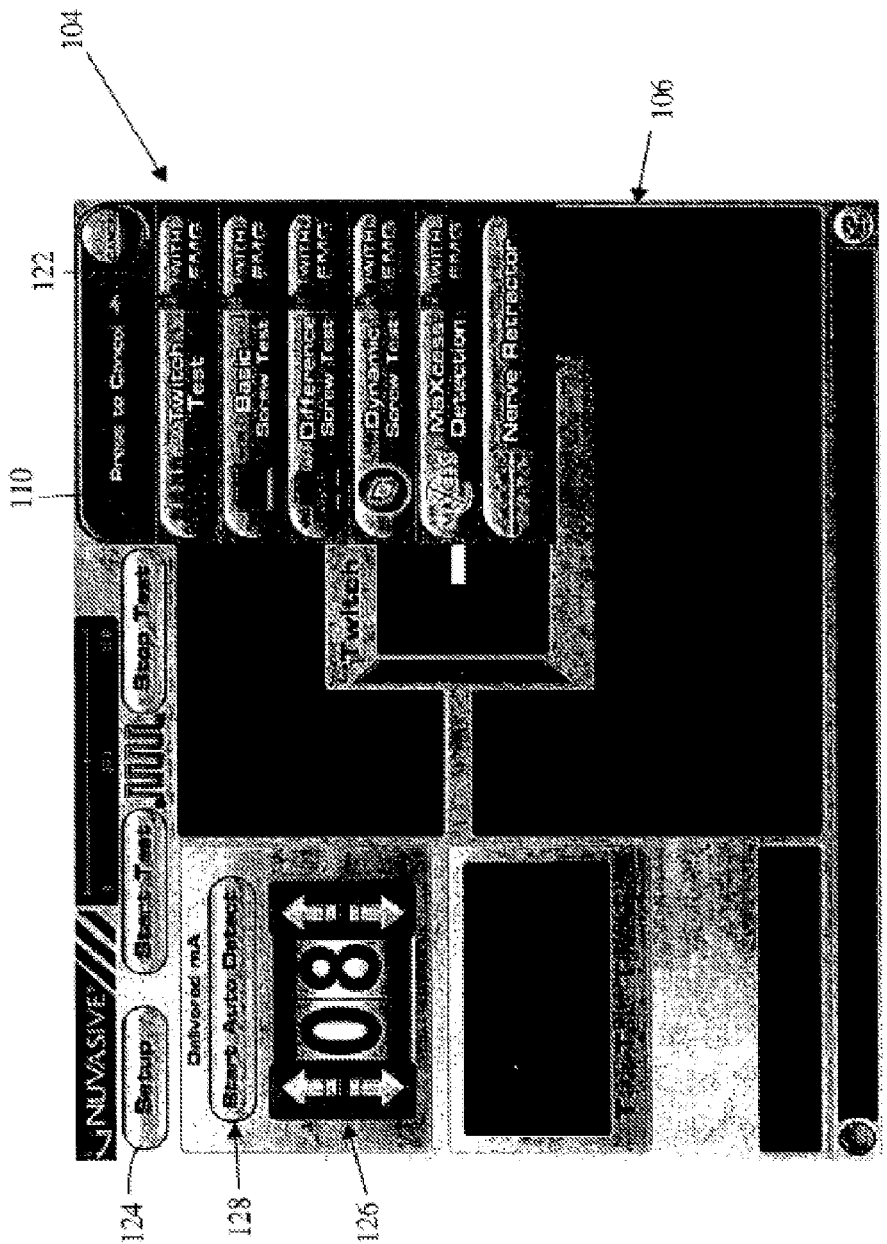
FIG. 3 is an exemplary screen display illustrating one embodiment of the of a drop down menu for navigating between different functions of the system 10 according to the present invention.

Switching between the various functions of the surgical system 10 may be accomplished from a drop down menu 104, which is preferably accessible from all screens on the GUI display 26. Selecting the menu button 118 labeled, by way of example only, "Select Mode" expands the drop down menu 104 as seen in FIG. 3. Using the menu 104 the surgeon or other qualified user may open any of the functions by selecting the function tab 110 corresponding to the desired function. Also from the menu 104, the user may optionally select to view the actual EMG waveforms 116 alongside the numerical result coinciding with a particular stimulation. This is accomplished by selecting an EMG tab 122 associated corresponding to the desired function. It should be understood that the drop down menu described above is only a preferred method of navigating between functions and any of a number of different methods may be used. By way of example only, a menu bar containing the different function buttons may be constantly displayed across the top or bottom of the screen.

Figure 4:
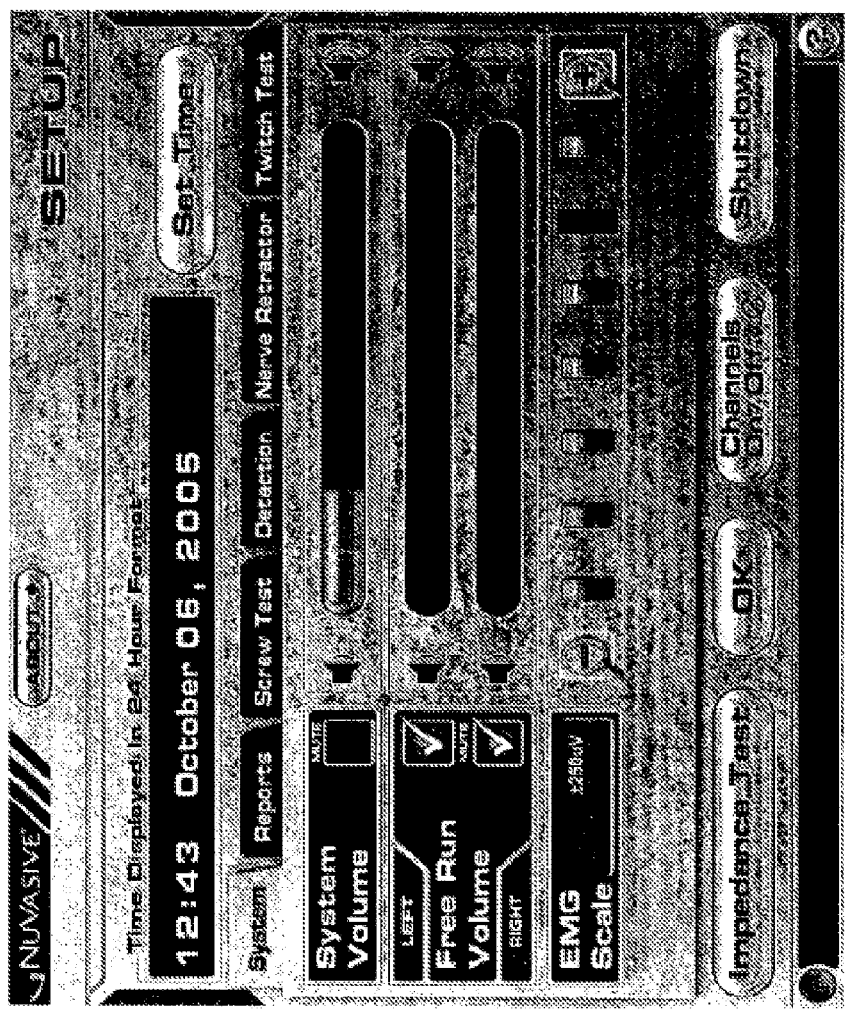
FIG. 4 is an exemplary screen display illustrating one embodiment of a general system setup screen.

A setup mode provides a simple means for selecting and/or changing various options and parameters associated with the functions of the surgical system 10. A setup tab 124 is provided on the GUI display 26 for accessing the setup mode, which preferably includes a separate setup screen for each function. FIG. 4 is an exemplary illustration, set forth by way of example only, of a general system setup screen. From the system set up screen the user may adjust the system volume, adjust the free run EMG volumes, change the EMG scale, turn different EMG channels on or off, set the date and time, conduct an impedance test to check the electrical connection between the EMG electrodes and the patients skin, and shutdown the system 10. The remaining setup screens will be shown and discussed below in conjunction with their associated functions.

In a preferred embodiment, the surgeon-directed surgical system 10 detects and monitors muscle activity using EMG (electromyogram). EMG monitoring is preferably carried out utilizing the same equipment and configuration for all the functions of the surgical system 10 and will now be described. EMG response monitoring is accomplished via 8 pairs of EMG electrodes 18 placed on the skin over the major muscle groups of the legs (four per side), a common electrode 20 providing a ground reference to pre-amplifiers in the patient module 14, and an anode electrode 20 providing a return path for the stimulation current. The EMG responses provide a quantitative measure of the nerve depolarization caused by the electrical stimulus. Depending on the particular function, analysis of the EMG responses is used to determine the status of the neuromuscular pathway (NMP), pedicle integrity, nerve proximity or nerve pathology. If peripheral nerve stimulation is chosen for the NMP test according to the present invention, it is preferably targeted to a nerve innervating one of the muscle groups to be monitored during the ensuing nerve tests. In doing so, one pair of EMG electrodes 18 is utilized during both NMP testing and the desired nerve testing, thereby eliminating the need for additional electrodes and recording channels. By way of example only, the placement of EMG electrodes 18 for spinal surgery may be undertaken according to the manner described in Table 2 below:

TABLE 2

| Color | Channel ID | Myotome | Nerve | Spinal Level |
|---|---|---|---|---|
| Red | Right 1 | Right Vastus Medialis | Femoral | L2, L3, L4 |
| Orange | Right 2 | Right TibialisAnterior | Peroneal | L4, L5 |
| Yellow | Right 3 | Right Biceps Femoris | Sciatic | L5, S1, S2 |
| Green | Right 4 | Right Gastroc. Medial | Post Tibialis | S1, S2 |
| Blue | Left 1 | Left Vastus Medialis | Femoral | L2, L3, L4 |
| Violet | Left 2 | Left Tibialis Anterior | Peroneal | L4, L5 |
| Gray | Left 3 | Left Biceps Femoris | Sciatic | L5, S1, S2 |
| White | Left 4 | Left Gastroc. Medial | Post Tibialis | S1, S2 |

Although not shown, it will be appreciated that any of a variety of electrodes can be employed, including but not limited to surface pad electrodes and needle electrodes. It should also be appreciated that EMG electrode placement has been shown and described, by way of example only, as it relates to use of the surgical system 10 during procedures in the lumbar spine. However, electrode placement depends on the surgical area and particular nerves at risk, and as such is not limited to the legs. By way of example, the surgical system 10 and its various functions may be utilized in the cervical and thoracic regions as well, wherein, it may be necessary to deploy the EMG electrodes 18 on the upper or mid regions of the body, respectively.

The surgical system 10 may perform NMP assessments by electrically stimulating a peripheral nerve via PNS electrodes 25 placed on the skin over the nerve and/or by direct stimulation of a spinal nerve using a surgical accessory such as screw test probe 36. Evoked responses from the muscles innervated by the stimulated nerve are detected and recorded, the results of which are analyzed and a relationship between at least two responses or a stimulation signal and a response is identified. The identified relationship provides an indication of the status of the NMP (e.g. blocked, unblocked, questionable). As discussed in greater detail below, the identified relationship may include, but is not necessarily limited to, one or more of magnitude ratios between multiple evoked responses and/or the presence or absence of an evoked response relative to a given stimulation signal or signals. Details of the test indicating NMP status and the relative safety of continuing on with nerve testing are conveyed to the surgeon via the screen display 26.

Figure 5:
FIG. 5 is an exemplary screen display illustrating one embodiment of a neuromuscular pathway test (a.k.a. "Twitch Test") setup screen providing for selection between Peripheral and Direct Stimulation modes according to the present invention.

According to one embodiment of the present invention, NMP testing may be carried out utilizing direct stimulation and/or peripheral stimulation. The decision to use the Direct or Peripheral Stimulation modes should be based on the particular needs, experience, and preferences of the operating surgeon. Choosing between the modes is preferably accomplished on the GUI display 26 from the Twitch Test setup screen, illustrated in FIG. 5. In direct stimulation mode a surgical accessory 32, such as screw test probe 36, is used to stimulate in the direct vicinity of a nerve in the surgical area of interest while evoked responses are monitored, preferably, via EMG electrodes 18. In peripheral stimulation mode, NMP testing may (by way of example only) be conducted on the Peroneal Nerve with evoked responses monitored from the Tibialis Anterior muscle. Accordingly, the PNS electrodes 25 are positioned on the skin above the Peroneal Nerve (preferably at the fibular head) and a corresponding pair of muscle activity sensors, such as EMG electrodes 18, are situated on the Tibialis Anterior. The NMP test is administered by delivering a stimulation signal (by having the surgeon activate a stimulation button on the hand piece 34), preferably consisting of four electrical pulses of equal current, through a surgical accessory 32 (direct stimulation mode) or PNS electrodes 25 (peripheral stimulation mode). Under normal body conditions (i.e., no NMB) the four electrical pulses each produce one muscle contraction or evoked response. As the neuromuscular pathway becomes inhibited by the neuromuscular blocking agents, the evoked responses diminish, beginning with the loss of the fourth response and continuing until no evoked responses occur, indicating a complete NMB.

Figure 6:
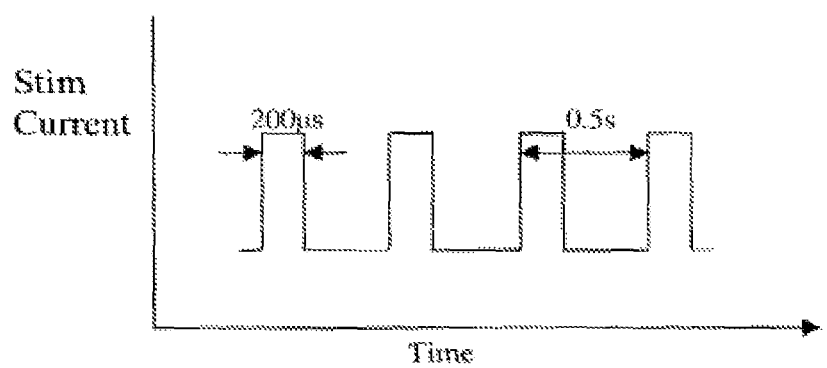
FIG. 6 is a is a graph illustrating a plot of four electrical stimulation pulses employed during the neuromuscular pathway assessment of the present invention.

FIG. 6 is a graphical illustration of an exemplary stimulation signal delivered by the surgeon-directed surgical system 10 during the NMP test. The electrical pulses may be delivered at a single frequency selected from a range of, by way of example only, 0.5 Hz to 5 Hz, and preferably a frequency of 2 Hz (0.5 s intervals) may be employed. Each pulse should last for an identical period of time (i.e. have the same pulse width) selected from a range of, by way of example only, 100 µs to 500 µs, with a preferred pulse width of 200 µs. The short pulse width is preferable because the Peroneal Nerve is stimulated in close proximity to the muscle it innervates, making direct stimulation of the muscle a concern in Peripheral Stimulation mode. However, nerve fibers are approximately four times more sensitive than muscle fibers and the short 200 µs pulses will diminish the possibility of bypassing the nerve and directly stimulating the muscle. This ensures that any muscle contraction recorded during the peripheral nerve stimulation is caused by transmission of a motor nerve impulse across the neuromuscular junction.

In one embodiment of the present invention, the stimulation pulses of the NMP test may be delivered at a supramaximal current, such that all the muscle fibers of the given muscle contract and the force of contraction is at its maximum level (in the absence of NMB). The level of current required to achieve a supramaximal effect varies between individual patients. Several factors including fluctuations in skin resistivity during a procedure, fat content, muscle mass, and muscle contractility, all may affect the current level necessary to achieve a supramaximal effect. Likewise, the voltage required to maintain the supramaximal current at the same level varies in response to the variations in resistance based on these factors. In one embodiment the surgical system 10 therefore determines an optimum current (hereinafter referred to as the "baseline current") to be used for each individual patient. In addition, the current output may be continually monitored and the voltage output adjusted so as to maintain the selected baseline current throughout the test.

Figure 7:
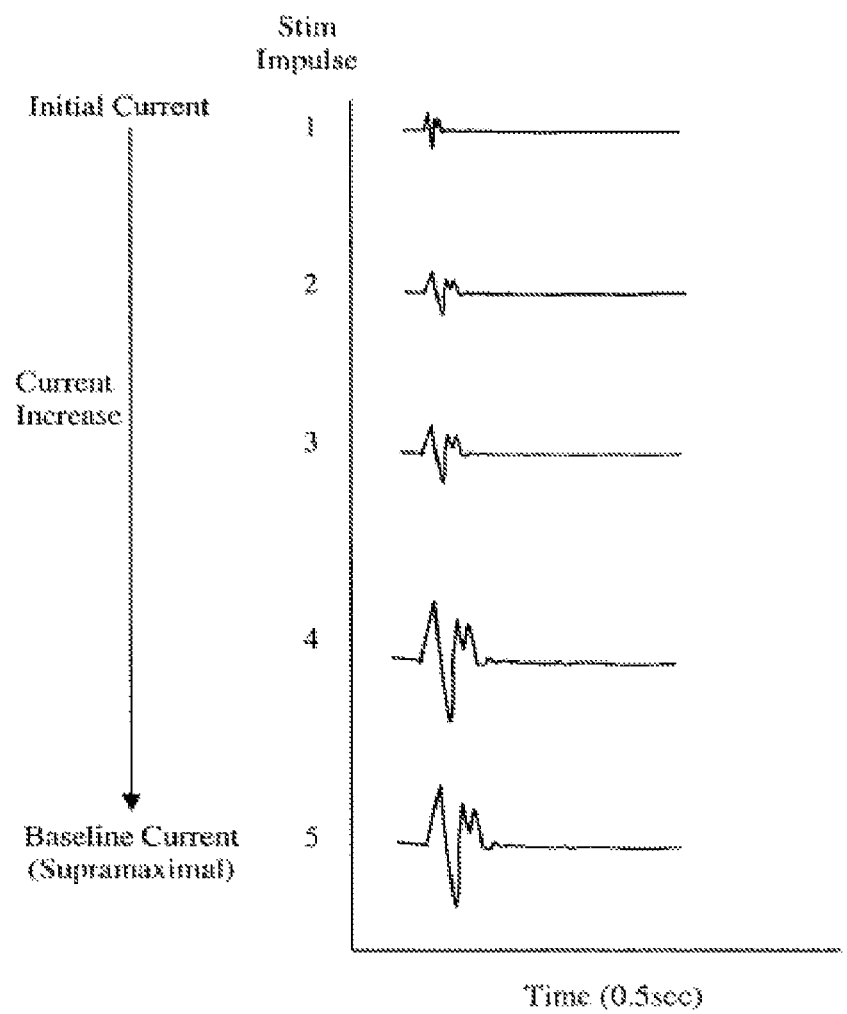
FIG. 7 is a graph illustrating a method of increasing stimulation current amplitude to determine a supramaximal current for use in the neuromuscular pathway (NMP) assessment of the present invention.

FIG. 7 illustrates one manner in which the baseline current may be determined. A baseline-setting test is initiated at the beginning of the surgical procedure, prior to the administration of any NMB. A stimulation pulse of the selected pulse width (preferably 200 µs) is delivered at an initial current (typically 20 mA) and the contraction force is measured and recorded by the system 10. A second pulse of the same pulse width but increased current magnitude is then delivered and the contraction force is again measured and recorded. This process may continue until the increase in current magnitude results in no additional increase in contraction force. This current magnitude, where no increase in contraction force occurs, may preferably be set as the baseline current. In addition, the surgical system 10 may allow the baseline to be set or reset manually at any time from the Twitch Test screen (FIGS. 11-12) on the touch screen display 26, thereby providing the surgeon or system operator with ultimate control over the baseline current if needed. In one embodiment, the baseline current is manually set by selecting up and down control arrows 126 to either increase or decrease the current level. This may be necessary, for example, if the baseline-setting test was not performed before administration of an NMB.

In another embodiment, the baseline current used for the NMP test may be such that it is slightly larger than the threshold current level ($I_{Thresh}$) at the time the NMP test is conducted. $I_{thresh}$ is the lowest stimulation current necessary to evoke an EMG response with a peak-to-peak voltage ($V_{pp}$) greater than a predefined threshold voltage ($V_{thresh}$) which is typically around 100 µV. To determine the stimulation current level to employ for the NMP test, the surgical system 10 may use a threshold-hunting algorithm to quickly and accurately find $I_{thresh}$. Preferably, upon selecting the Auto Detect tab 128, the system 10 detects $I_{thresh}$ using a threshold-hunting algorithm that applies bracketing and bisection methods which are described in detail below. Once $I_{thresh}$ has been determined the surgical system 10 may display $I_{thresh}$ for the user and/or select a baseline current that is greater than $I_{thresh}$, which may similarly be displayed for the surgeon. According to one embodiment, set forth by way of example only, this baseline current determination may be accomplished by adding at least 1.0 mA to $I_{thresh}$.

After setting a baseline current, the baseline current may subsequently be used any time the NMP test is conducted during a surgical procedure (i.e. prior to initiating the nerve monitoring tests, discussed in detail below) or a new baseline may be determined each time. As previously mentioned, an exemplary NMP test consists of four 200 µs electrical impulses, delivered at a frequency of 2 Hz and at the determined baseline current. When the test is completed in the presence of little or no NMB, the muscle activity pattern contains four clearly defined muscle contractions of approximately the same amplitude, illustrated, by way of example only, in FIG. 8. As the NMB level increases, the contractions diminish in amplitude and disappear in reverse order beginning with the fourth contraction, illustrated, by way of example only, in FIGS. 9-10.

According to one embodiment of the present invention, the surgeon-directed surgical system 10 identifies a ratiometric relationship between evoked responses to assess the status of the NMP. The amplitudes of each EMG response corresponding to the four electrical pulses (described above with reference to FIG. 6) are monitored and recorded by the system 10. In one embodiment, the amplitude of the EMG response is defined by a peak-to-peak voltage of the response as discussed in more detail below. The value T1 equals the amplitude of the first muscle response, T2 is the amplitude of the second muscle response, T3 is the amplitude of the third response, and T4 is the amplitude of the fourth muscle response. Once values T1 through T4 are measured the system calculates the amplitude ratio between T4 and T1. The T4:T1 ratio provides an indication of the functioning capability of the NMP.

Figure 11:
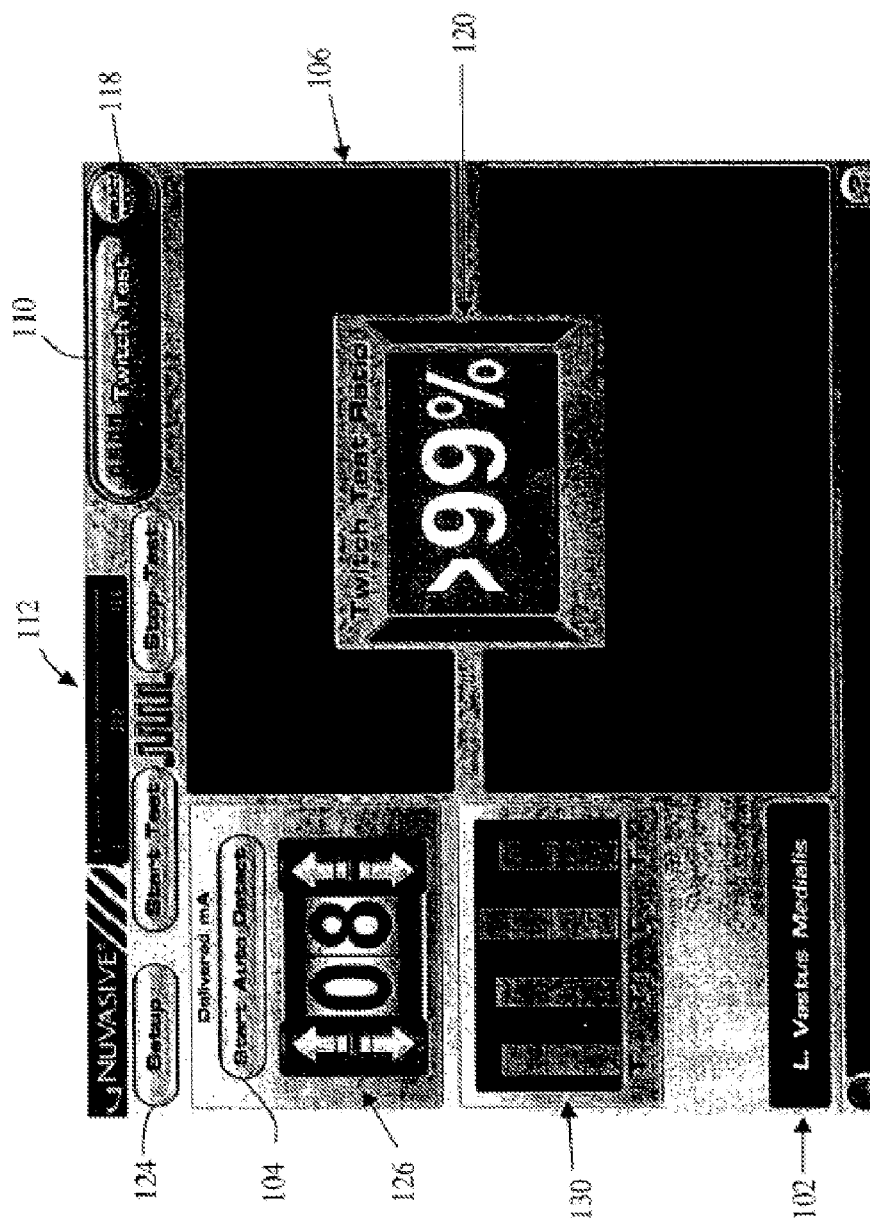
FIGS. 11-12 are exemplary screen displays illustrating various embodiments of the NMP test function according to the present invention.
Figure 12:
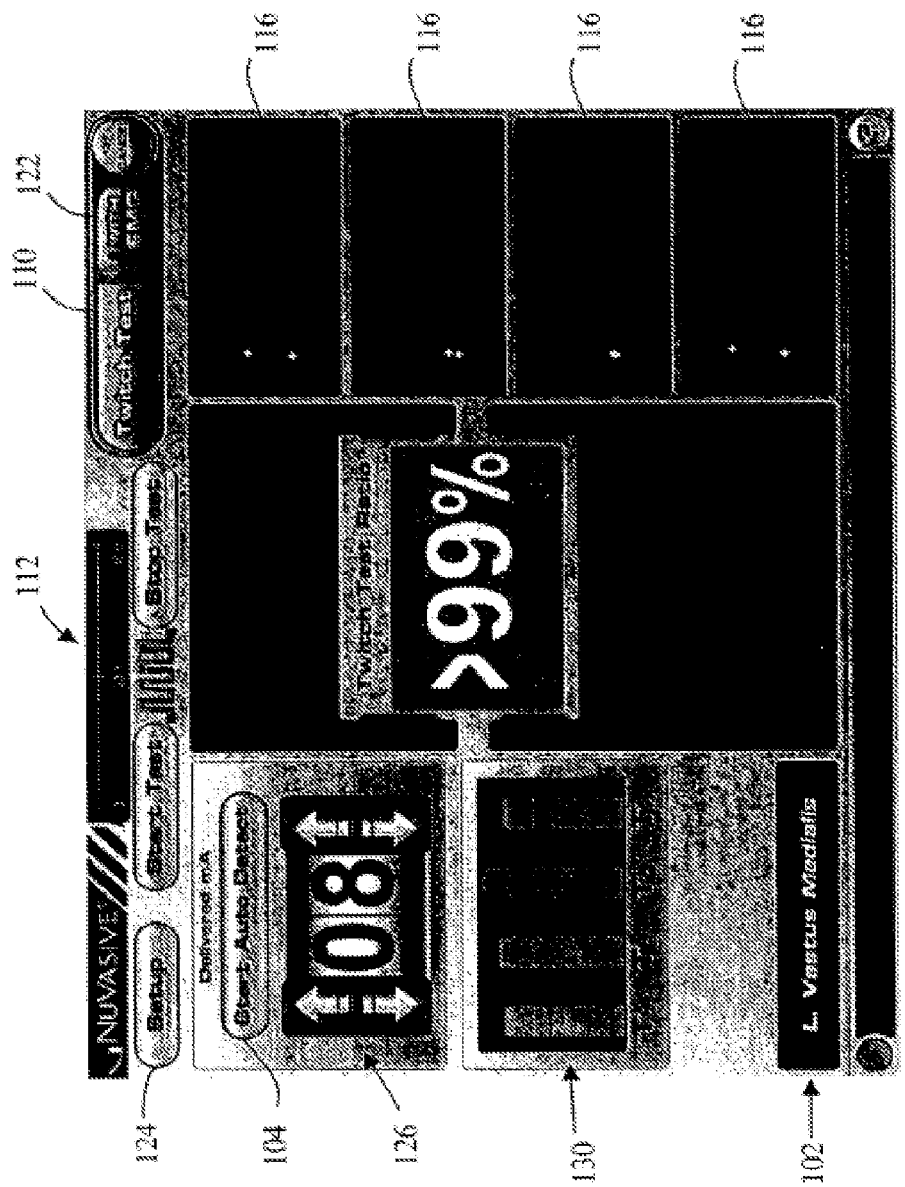

FIGS. 11-12 are exemplary screen displays, set forth by way of example only, of one embodiment of the twitch test function. The T4:T1 ratio is calculated and displayed to the user. In a preferred embodiment the T4:T1 ratio is displayed to the user in terms of the percentage of T4 to T1, as illustrated. In addition to the numerical result 120, the colors Red, Yellow, and Green are preferably displayed to indicate to the surgeon the level of safety determined by the system 10 during the NMP test. By way of example only, the color red may be displayed when the T4:T1 ratio is determined to be below a predetermined alert level of, by way of example, 0.3 or 30%. Green may be displayed when the T4:T1 ratio is above the predetermined safe level, by way of example only 0.75 or 75%. Finally, the color yellow may be displayed when the T4:T1 ratio falls between the predetermined alert level and a predetermined safe level (ie. between 30% and 75%). Also shown in FIG. 11-12 is a bar graph 130 depicting the relative T1 through T4 response levels, which is preferably displayed to the user along with the numerical result 120. FIG. 11 is an example of the twitch test display without the optional EMG waveforms 116 and FIG. 12 shows the twitch test display with the optional EMG waveforms 116 selected.

Although use of the system 10 for neuromuscular pathway assessment is shown and described above within the context of particular exemplary method of stimulation response analysis, it will be appreciated by those skilled in the art that a variety of methods may be employed by the system 10, for stimulating a nerve and analyzing the resultant muscle response or responses in order to determine the state of the neuromuscular pathway, and as such, fall within the scope of the present invention. These methods may include, but are not necessarily limited to the all-or-none and single twitch techniques described below.

Figure 8:
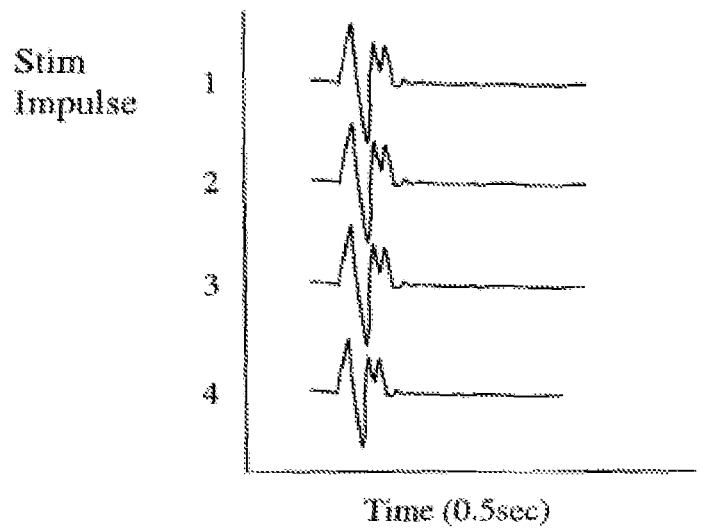
FIG. 8 is a graph illustrating an exemplary EMG response to the stimulus of FIG. 6 in the presence of little or no neuromuscular blockade (NMB).
Figure 9:
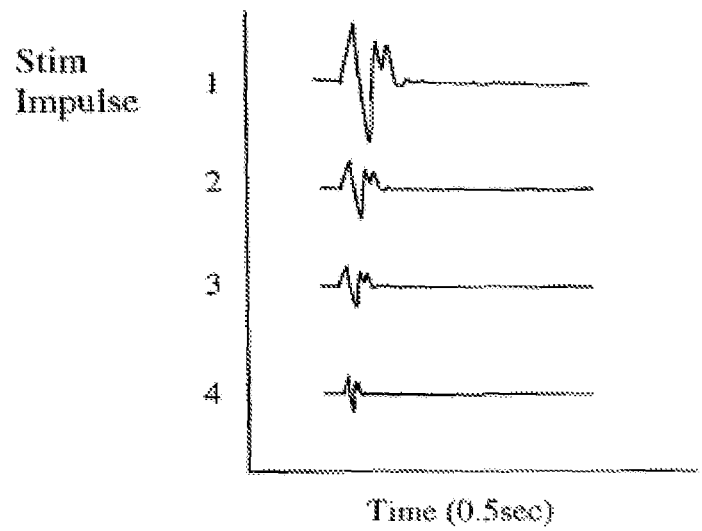
FIG. 9 is a graph illustrating an exemplary EMG response to the stimulus of FIG. 6 wherein the fourth response is present but diminished.
Figure 10:
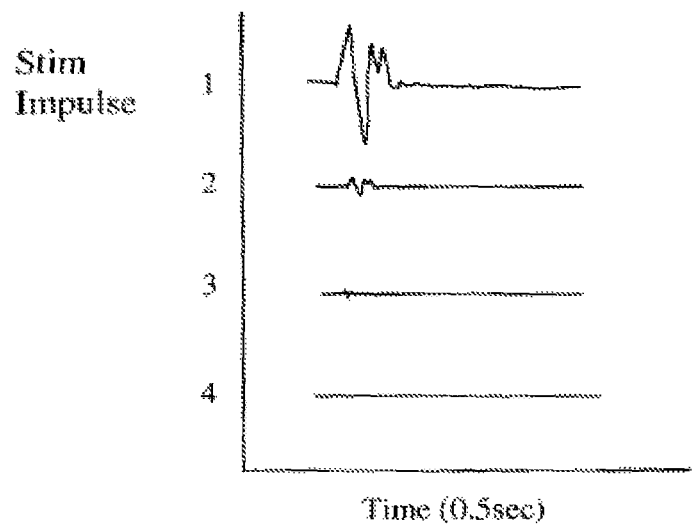
FIG. 10 is a graph illustrating an exemplary EMG response to the stimulus of FIG. 6 wherein the fourth response has disappeared completely.

In an alternate embodiment, the disappearance of each response corresponds to particular level of NMB. By way of example only, the fourth contraction disappears at a 75% NMB level (meaning that 75% of the acetylcholine receptors are occupied), the third contraction disappears at 80% NMB (meaning that 80% of the acetylcholine receptors are occupied), the second disappears at 90% NMB (meaning that 90% of the acetylcholine receptors are occupied), and the first contraction disappears at 100% NMB level (meaning that 100% of the acetylcholine receptors are occupied). In one embodiment of the present invention, detection of an NMB level greater than 75%, (i.e. less than four contractions detected, corresponding to the four electrical impulses) as depicted in FIG. 10, is considered an unsafe level. An acceptable NMB level of below 75% is indicated by an EMG response including all four muscle contractions (FIGS. 8-9). At this level of NMB, less than 75%, it is unlikely that a muscle will fail to contract in response to stimulation during the nerve monitoring tests.

In still another embodiment, the surgeon-directed surgical system 10 may employ a "single twitch" method for assessing the neuromuscular pathway. A baseline supramaximal current is again determined by the method set forth and described above. After determining the baseline and still prior to the administration of NMB, a single 100 µs-300 µs (preferably 200 µs) electrical pulse of the baseline current is delivered to the patient via the surgical system 10 and the muscle response is measured. The amplitude of the measured response is the control value or T0 for subsequent NMP tests. NMP tests are later initiated in the selected mode (Direct or Peripheral stimulation) with a single electrical impulse identical to the pulse used to obtain T0 and the evoked muscle response is measured. The measured amplitude of the response becomes T1. The system 10 calculates the amplitude ratio between T0 and T1 (T1:T0) and compares it to predetermined safe and unsafe levels. By way of example only, when T1:T0 is greater than or equal to 0.9 (T1:T0≥0.9) the NMP test is acceptable and the display 26 indicates the safe result. When the T1:T0 ratio is less than 0.9 (T1:T0<0.9) the NMP is determined to unsafe (blocked) and the result is again indicated on the display 26, thereby alerting the surgeon to the unsafe NMP status.

While the NMP function has been described according to a preferred embodiment in which evoked muscle responses are detected using EMG, it is contemplated that other methods of detecting and measuring evoked responses may also be employed. In an alternate embodiment, set forth by way of example only, the surgical system 10 may use pressure sensors (not shown) communicatively linked to the system, to monitor muscle activity. An increase in pressure detected by the pressure sensors deployed over various muscles or myotomes indicates a muscle response. The magnitude of the response is reflected by the degree of pressure change detected. The evoked responses may then be analyzed to identify a relationship between them according to one or more of the methods described above thereby providing an indication of the NMP status.

The surgeon-directed surgical system 10 is capable of performing pedicle integrity tests, preferably after an NMP test has been conducted and deemed acceptable and safe. This functionality includes a "Basic" screw test and a "Dynamic Screw Test." The basic, or static, screw test function is performing using screw test probe 36. The screw test probe 36 is used to test the integrity of pedicle holes (during and/or after formation) and/or screws (during and/or after introduction). The screw test probe 36 includes a stimulation handpiece 34 and a probe member 38 having a generally ball-tipped end 40.

The handpiece 34 may be equipped with one or more buttons for selectively applying the electrical stimulation to the ball-tipped end 40 at the end of the probe member 38. The ball tip 40 of the screw test probe 36 is placed in the screw hole prior to screw insertion or placed on the installed screw head. The insulating character of bone will prevent the stimulation current, up to a certain amplitude, from communicating with the nerve. However, in the event the pedicle wall has been breached by the screw or tap, the stimulation current will pass through to the adjacent nerve roots and they will depolarize at a lower stimulation current.

The "Dynamic" screw test function may use at least one of an electric coupling device 42 and 52. The probe member 38 and the ball-tipped end 40 of screw test probe 36 may be removed from the stimulation handpiece 34 and replaced with an electric coupling device 42, 52. The electric coupling devices 42, 52 may be utilized to couple a surgical instrument, such as for example only, a tap member 72, pedicle access probe 74, or other similar instrument, to the surgical system 10. By this means, a stimulation signal may be passed through the surgical instrument and screw testing can be performed while the tool is in use. Thus, screw testing may be performed during pilot hole formation by coupling the tap member 72 or pedicle probe 74 to the surgical system 10. Likewise, by coupling a pedicle screw to the surgical system 10, screw testing may be performed during screw introduction.

The electric coupling device may comprise a number of possible embodiments which permit the device to attach and hold a surgical instrument while allowing transmission of a stimulation signal to the tool. One such electric coupling device 42 utilizes a spring-loaded plunger to hold the surgical tool and transmit the stimulation signal. The plunger 44 is composed of a conductive material such as metal. A nonconductive housing 46 partially encases the plunger 44 about its center. Extending from the housing 46 is an end plate 48. An electrical cable 50 connects the electric coupling device 42 to the stimulation handpiece 34. A spring (not shown) is disposed within the housing 46 such that in a natural or "closed" state the plunger 44 is situated in close proximity to the endplate 42. Exerting a compressive force on the spring (such as by pulling the cable 50 while holding the housing 46) causes a gap between the end plate 48 and the plunger 44 to widen to an "open" position, thereby allowing insertion of a surgical tool between the end plate 48 and plunger 44. Releasing the cable 50 allows the spring to return to a "closed" position, causing the plunger 44 to move laterally back towards the endplate such that a force is exerted upon the surgical instrument and thereby holds it in place between the endplate 48 and the plunger 44. Thereafter the electrical stimulus may be passed from the handpiece 34 through the cable 50 and plunger 44 to the surgical instrument.

Alternatively, the electrical coupling device may be embodied in the form of a clip 52. The clip 52 is comprised of two prongs hingedly coupled at a coupling point 54 such that the clip 52 includes an attachment end 56 and a non-attachment end 58. A stimulation electrode 60 is disposed on the attachment end 56 and communicates with electric cable 50 extending from the non-attachment end 56 to the handle 34. In a "closed" position the prong ends at the attachment end 56 touch. Depressing the prongs at the non-attachment end 58 in a direction towards each other causes a gap to form between the prong ends at the attachment end 56. Positioning the "opened" attachment end 56 over a desired surgical instrument and releasing the force on the non-attachment end 58 causes the attachment end 56 to pinch tight on the surgical instrument and thereby allow the electrical stimulus to pass from the screw test handle 34, through the stimulation electrode 60, to the surgical instrument.

Figure 13:
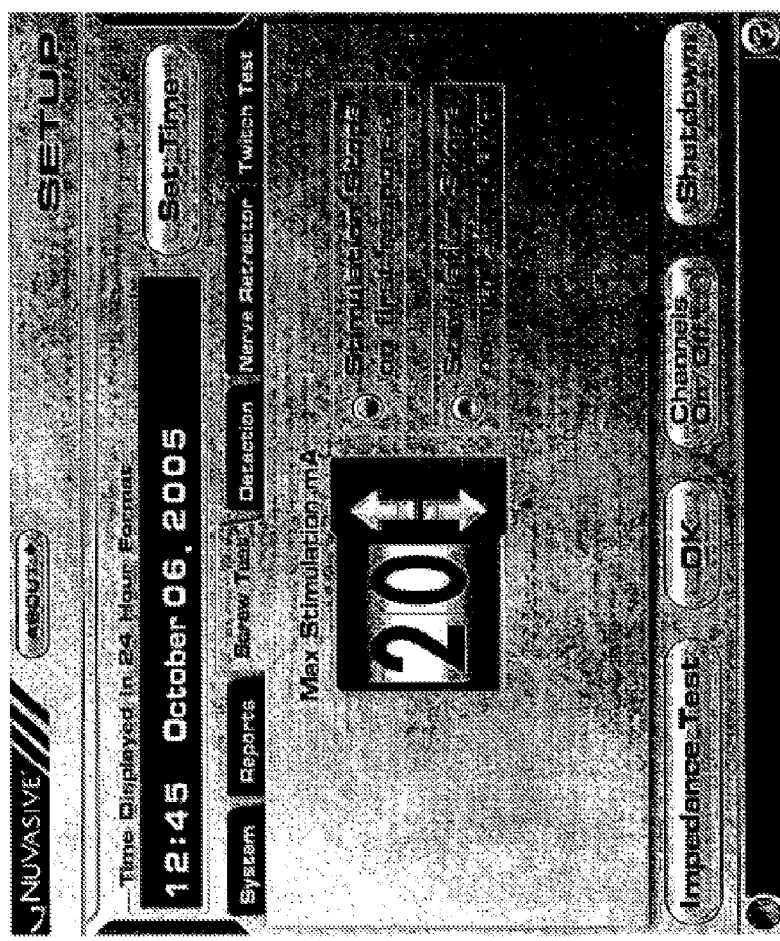
FIG. 13 is an exemplary screen display illustrating one embodiment of a screw test setup screen according to the present invention.

FIG. 13 depicts an exemplary setup screen for the screw test functions. From the setup screen the user may select to have stimulation signals stop on the first response or to continue until a maximum current level is reached. The maximum stimulation current may also be changed using the "up" and "down" control arrows 126 to increase or decrease the current level. In addition, the user may turn different EMG channels on or off, set the date and time, conduct an impedance test to check the electrical connection between the EMG electrodes and the patient's skin, and shutdown the system 10.

Upon pressing the button on the stimulation handpiece 34, the software will execute an algorithm (discussed below) that results in all channel tabs 132 being color-coded to indicate the detection status of the corresponding nerve. The algorithm preferably determines the depolarization (stimulation threshold current, $I_{thresh}$) current for all 8 EMG channels. The channel with the "worst" (lowest $I_{thresh}$) level will be highlighted (enlarged) and that myotome name will be displayed 102, as well as graphically depicted on the spine diagram 100 and the numerical stimulation result ($I_{thresh}$) 120 for that channel is displayed, as illustrated in FIGS. 14-19. EMG channel tabs 132 may also be selected via the touch screen display 26 to show the $I_{thresh}$ of the corresponding nerves. A vertical stimulation bar chart 112 is shown, to depict the stimulation current required for nerve depolarization in mA for the selected channel. The handpiece 34 may be equipped with a mechanism (via hardware and/or software) to identify itself to the system when it is attached. In one embodiment, the probe member 38 is disposable and the handpiece 34 is reusable and autoclavable.

Figure 14:
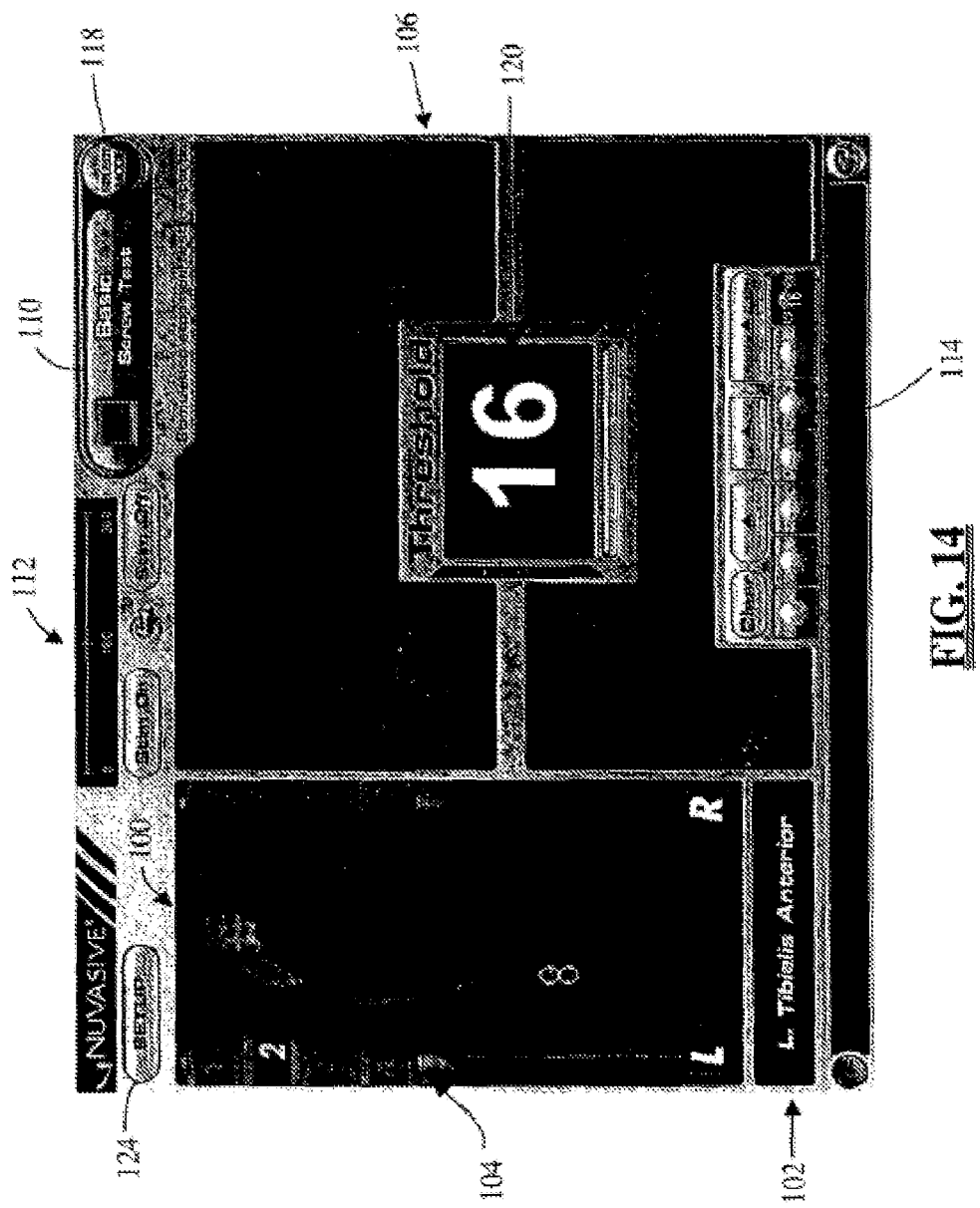
FIG. 14-15 are exemplary screen displays illustrating various embodiments of the Basic Screw Test function according to the present invention.
Figure 15:
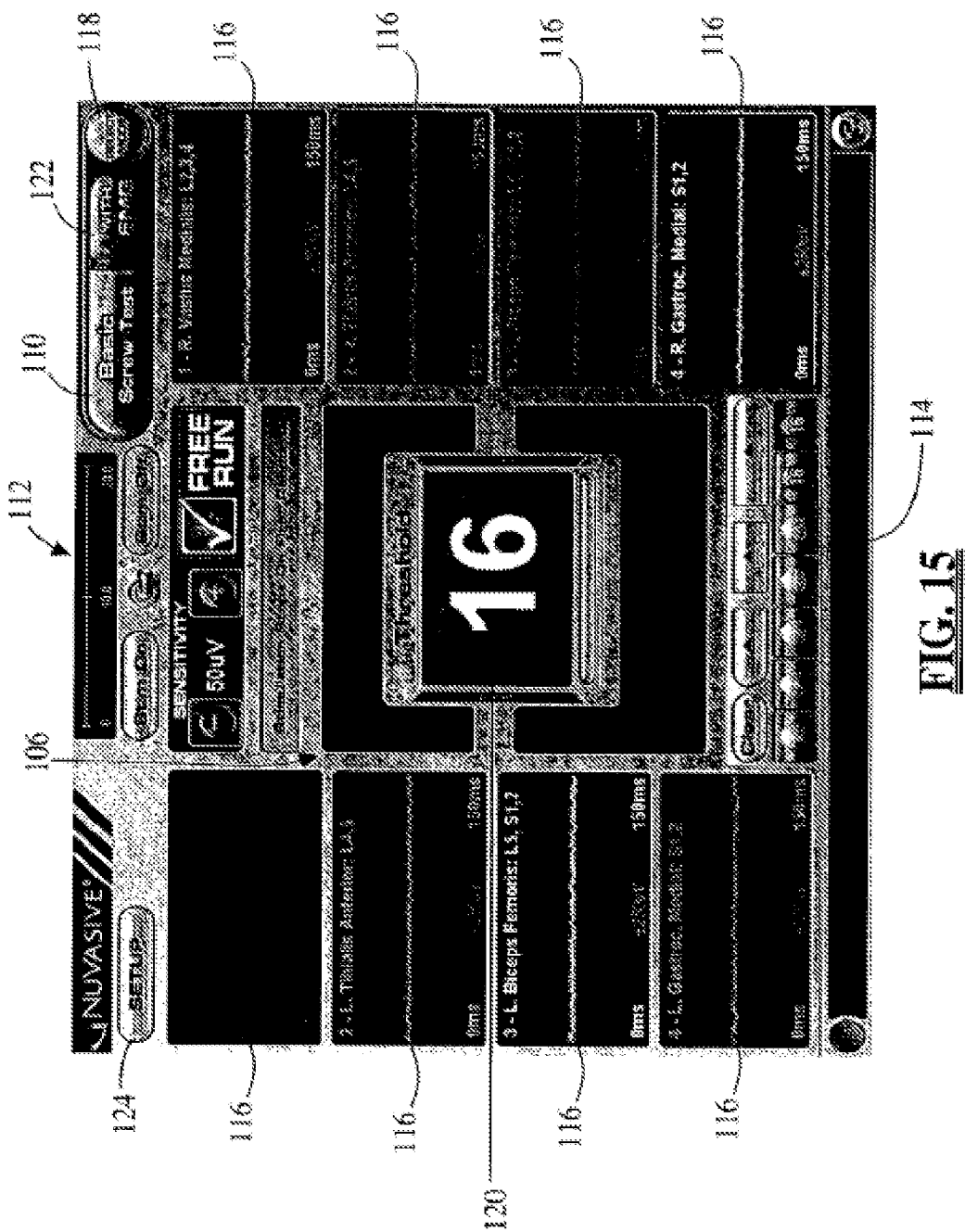
Figure 16:
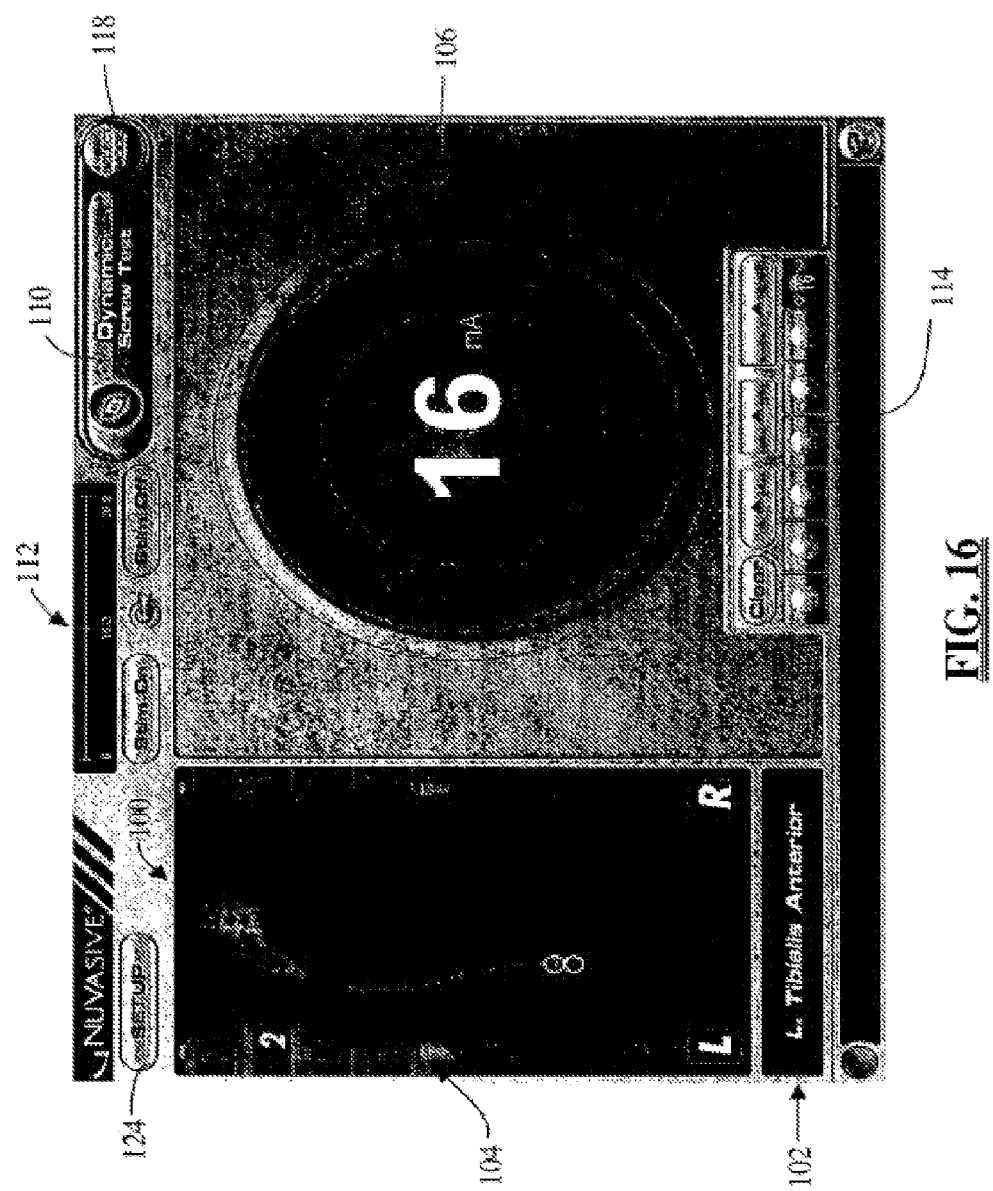
FIG. 16-17 are exemplary screen displays illustrating various embodiments of the Basic Screw Test function according to the present invention.
Figure 17:
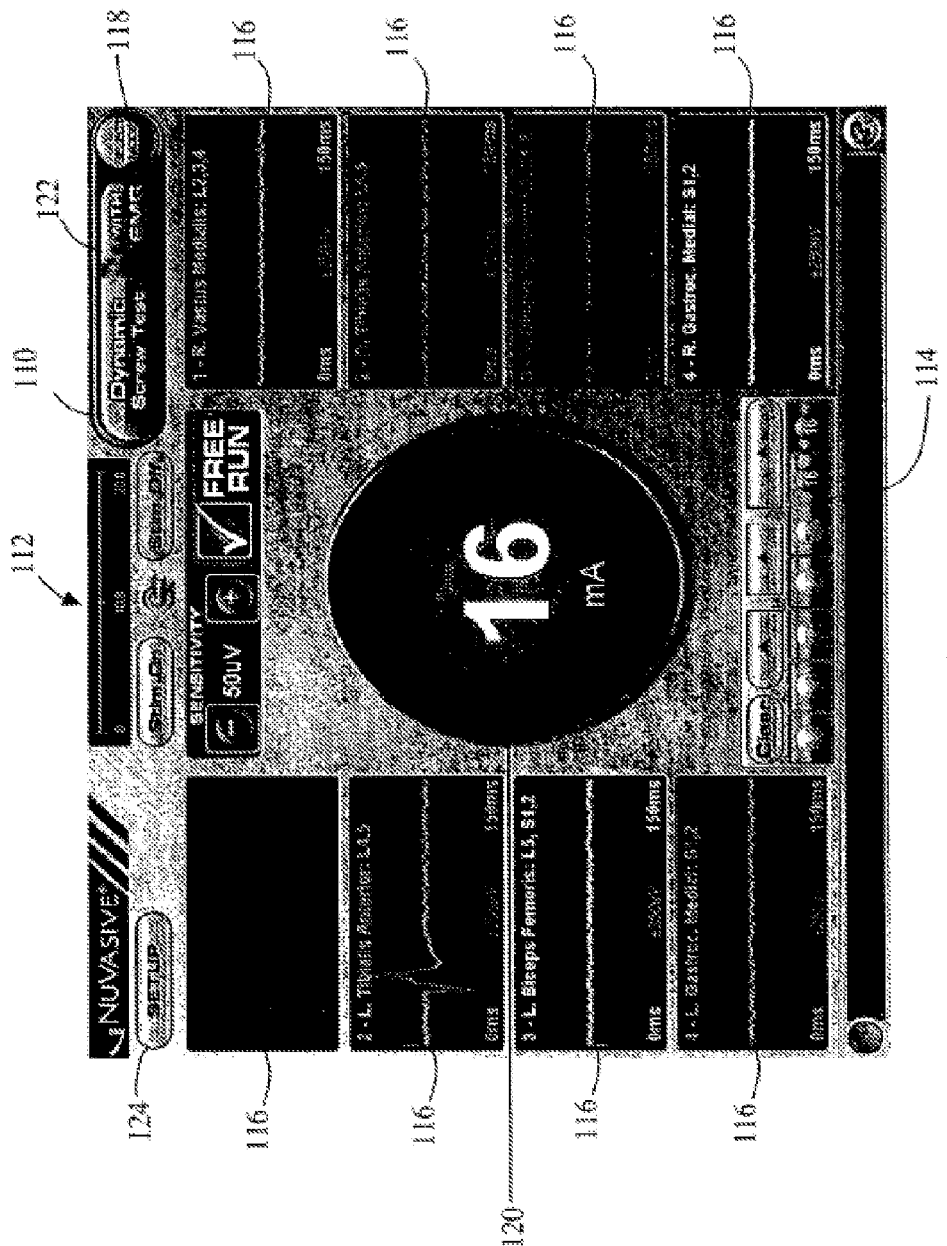
Figure 18:
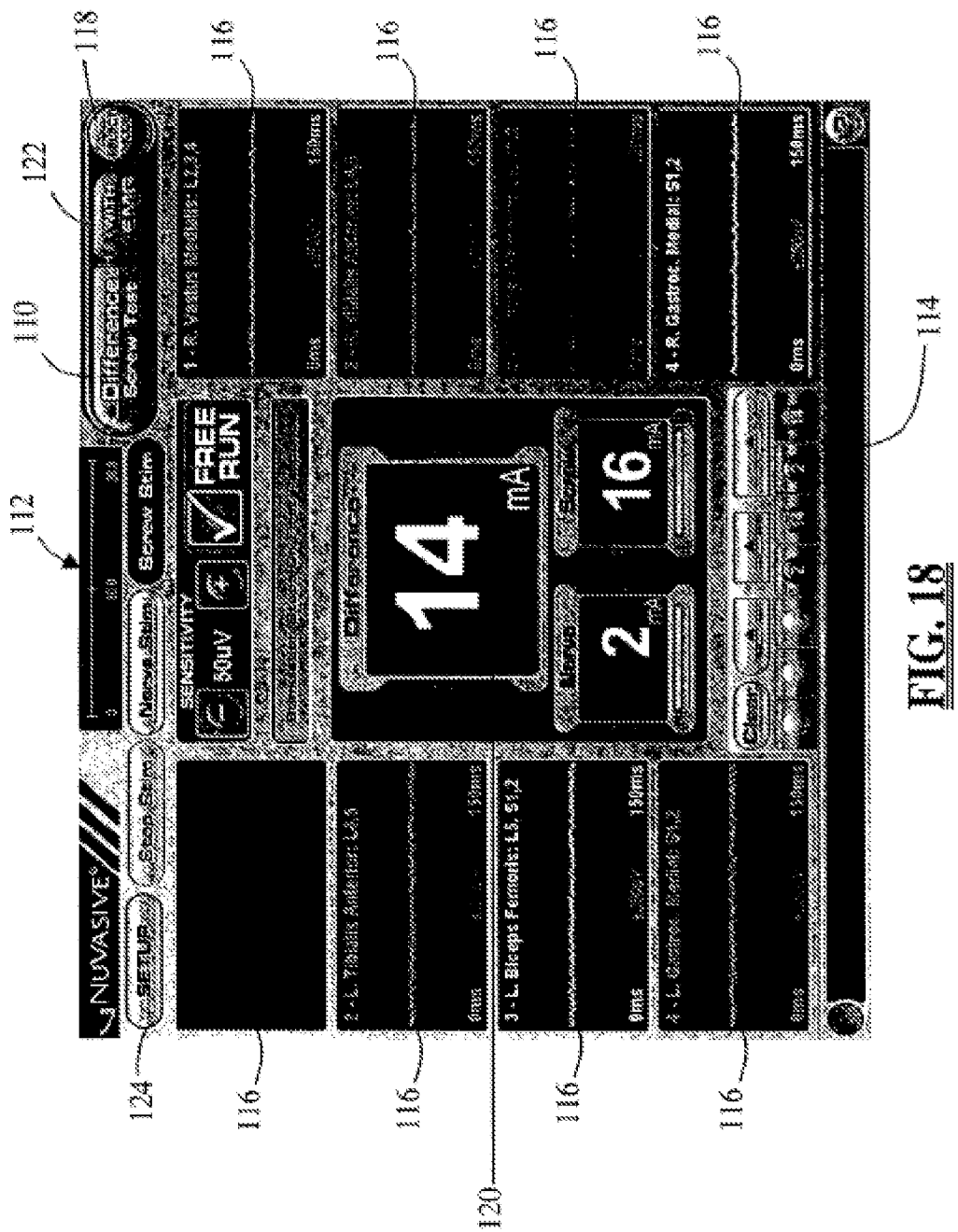
FIG. 18-19 are exemplary screen displays illustrating various embodiments of the Difference Screw Test function according to the present invention.
Figure 19:
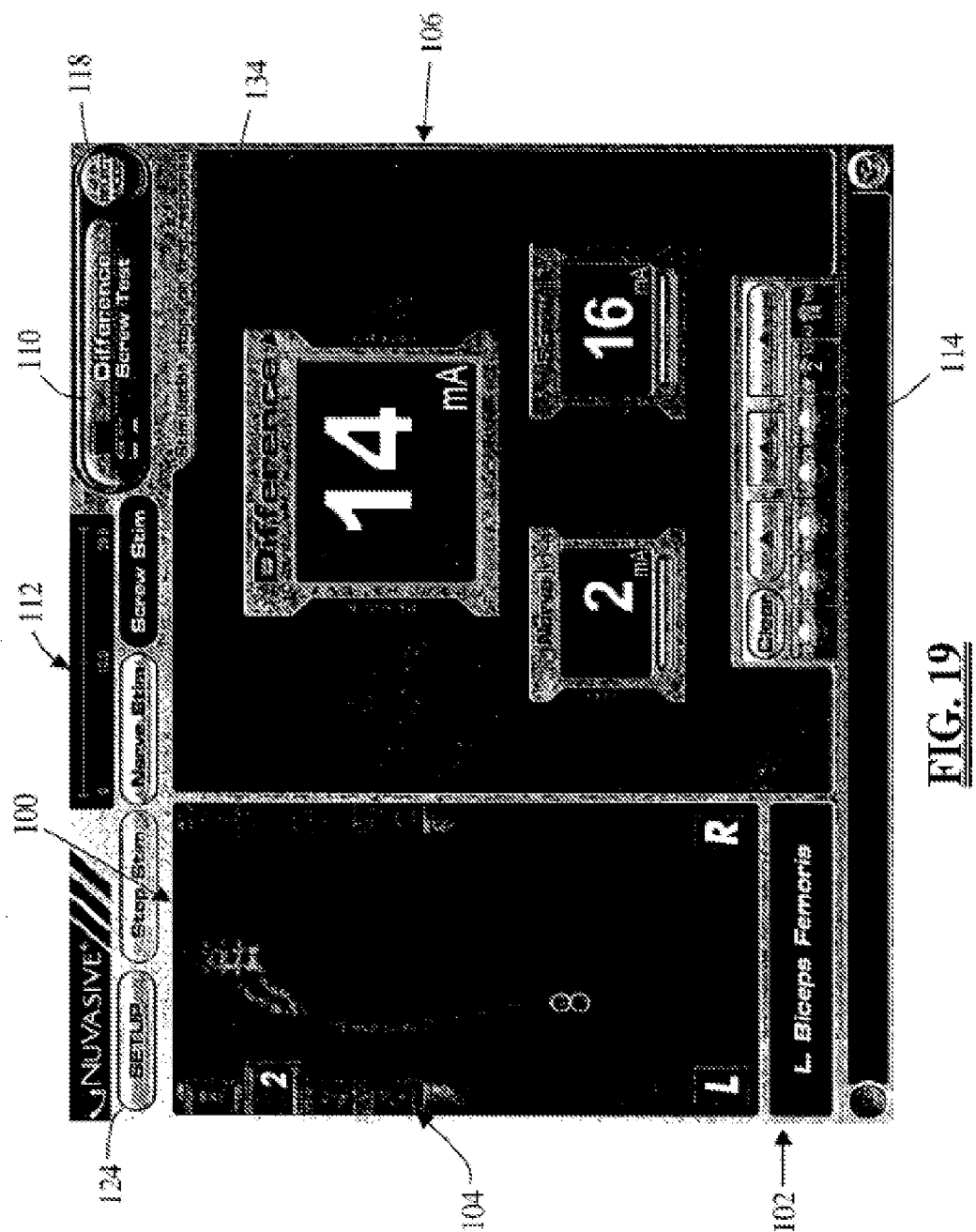

FIGS. 14-15 depict screen displays, shown by way of example only, for the Basic Screw Test function, one without optional EMG waveforms 116 (FIG. 14) and one with the optional EMG waveforms 116 (FIG. 15). FIGS. 16-17 depict screen displays shown by way of example only, for the Dynamic Screw Test function, again, one without optional EMG waveforms 116 (FIG. 16) and one with the optional EMG waveforms 116 (FIG. 17). Finally, FIGS. 18-19 depict screen displays, shown by way of example only, for the Difference Screw Test function, one without optional EMG waveforms 116 (FIG. 18) and one with the optional EMG waveforms 116 (FIG. 19). For the Difference Screw Test, the surgeon sets a baseline threshold 134 current by stimulating a nerve root directly with the screw test probe 36. The actual threshold current 136 is then determined and displayed relative to the baseline providing a difference threshold 138. In one embodiment, the stimulation result is displayed to the surgeon along with a color code so that the surgeon may easily comprehend the situation and avoid neurological impairment to the patient. The colors Red, Yellow, and Green are preferably displayed to indicate to the surgeon the level of safety determined by the system 10. Red is used to indicate an $I_{thresh}$ level below a predetermined unsafe level. Yellow indicates an $I_{thresh}$ that falls in between predetermined safe and unsafe levels. Green represents an $I_{thresh}$ within the range predetermined as safe. By way of example only, a green display denotes a stimulation threshold range of 9 milliamps (mA) or greater, a yellow display denotes a stimulation threshold range of 6-8 mA, and a red display denotes a stimulation threshold range of 6 mA or below.

The surgeon-directed surgical system 10 may provide safe and reproducible access to a surgical target site by detecting the existence of (and optionally the distance) neural structures before, during, and after the establishment of an operative corridor through (or near) any of a variety of tissues having such neural structures which, if contacted or impinged, may otherwise result in neural impairment for the patient. The surgical system 10 does so, preferably after an acceptable NMP test has been completed, by electrically stimulating nerves via one or more stimulation electrodes at the distal end of the surgical access components 62-66 while monitoring the EMG responses of the muscle groups innervated by the nerves. In a preferred embodiment the access components are coupled to the surgical system 10 using electrical coupling device 42 or 52 in the same manner described above. Alternatively, a stimulator driver 68 is provided to electrically couple the surgical access components 62-66 to the patient module 14 (via accessory cable 30). The stimulator driver 68 preferably includes one or more buttons for selectively activating the stimulation current and/or directing it to a particular surgical access component.

The surgical access components 62-66 (FIG. 1) are designed to bluntly dissect the tissue between the patient's skin and the surgical target site. An initial dilating cannula 64 is advanced towards the target site, preferably after having been aligned using any number of commercially available surgical guide frames. An obturator (not shown) may be included inside the initial dilator 64 and may similarly be equipped with one or more stimulating electrodes. Once the proper location is achieved, the obturator (not shown) may be removed and the K-wire 62 inserted down the center of the initial dilating cannula 64 and docked to the given surgical target site, such as the annulus of an intervertebral disc. Cannulae of increasing diameter are then guided over the previously installed cannula 64 until the desired lumen is installed. By way of example only, the dilating cannulae 64 may range in diameter from 6 mm to 30 mm. The working cannula 66 is installed over the last dilating cannula 64 and then all the dilating cannulae 64 are removed from inside the inner lumen of the working cannula 66 to establish the operative corridor therethrough.

Additional and/or alternative surgical access components such as, by way of example only, a tissue retraction assembly 70 (FIG. 1) may be coupled to the system 10 and employed to provide safe and reproducible access to a surgical target site. Tissue retraction assembly 70 and various embodiments and uses thereof have been shown and described in the above referenced co-pending and commonly assigned U.S. patent application Ser. No. 10/967,668, entitled "Surgical Access System and Related Methods," filed on Oct. 18, 2004, the entire contents of which are expressly incorporated by reference as if set forth herein in their entirety.

Figure 20:
FIG. 20 is an exemplary screen display illustrating one embodiment of a Detection setup screen according to the present invention.
Figure 21:
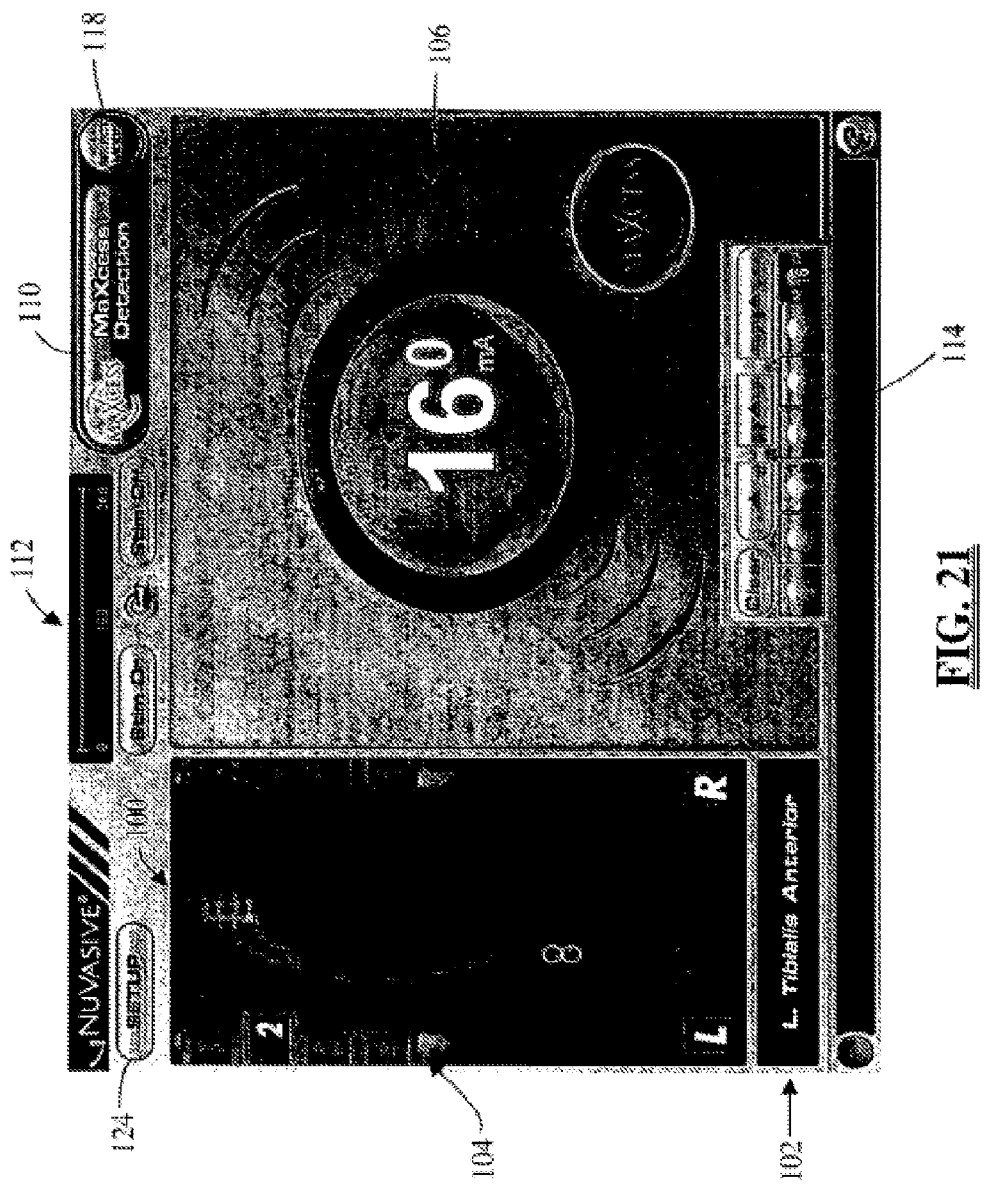
FIG. 21-22 are exemplary screen displays illustrating various embodiments of the Nerve Detection function according to the present invention.
Figure 22:
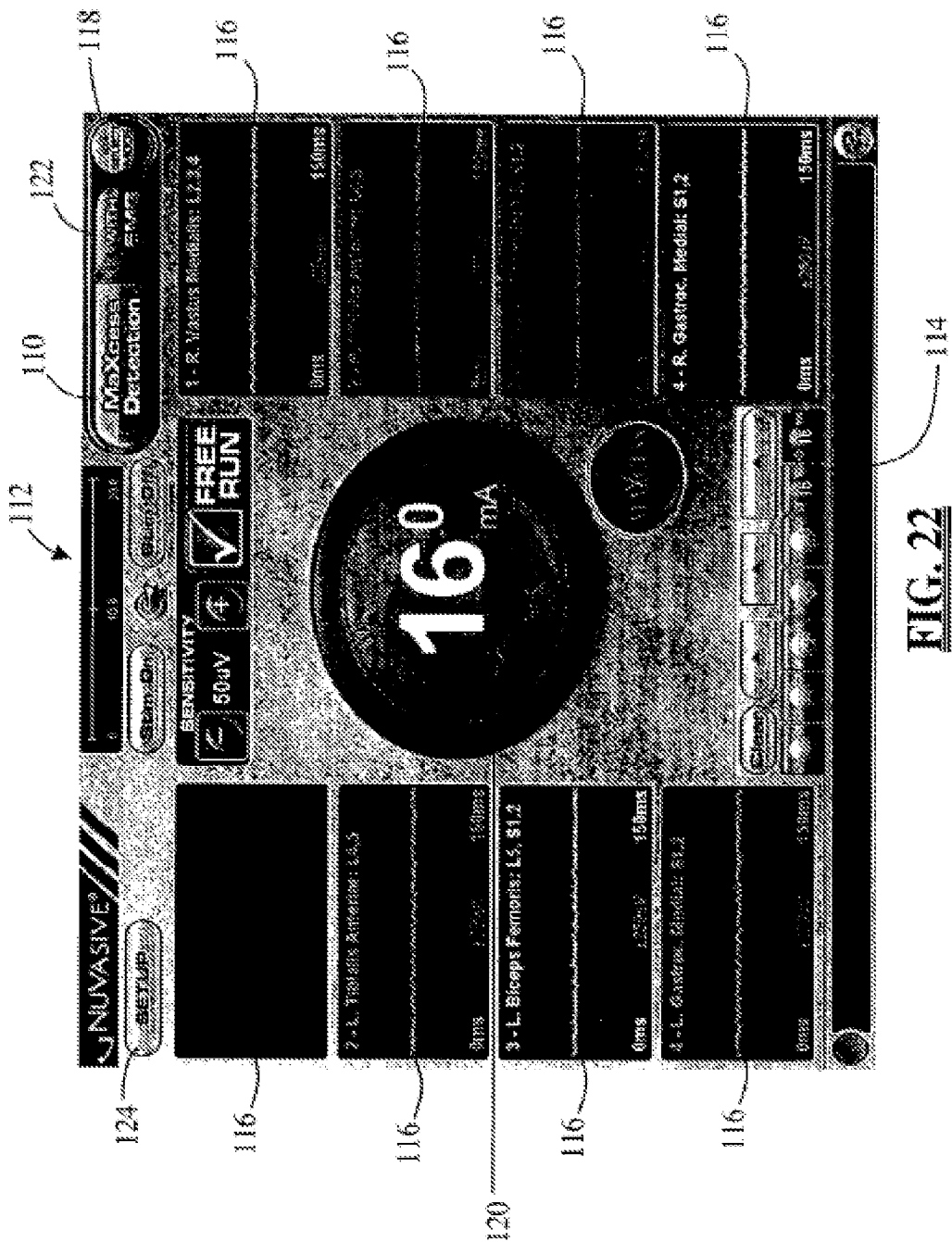

FIG. 20 depicts, by way of example only, a setup screen for nerve detection. Using this screen the operator may change the maximum stimulation current using up and down control arrows 126 to increase or decrease the current level, turn different EMG channels on or off, set the date and time, conduct an impedance test to check the electrical connection between the EMG electrodes and the patients skin, and shutdown the system 10. FIGS. 21-22 depict exemplary screen displays of the detection function. The function indicator tab 110 indicates that detection is the selected function. The EMG channel possessing the lowest stimulation result 120 may be automatically highlighted and/or colored to clearly indicate this fact to the surgeon. Additionally, EMG channel tabs 132 may be selected via the touch screen display 26 to show the result 120 of the corresponding nerves. As with the NMP and Screw Tests, the stimulation results are displayed to the surgeon with the Red, Yellow, Green color code wherein Red, Yellow, and Green are preferably displayed to indicate to the surgeon the level of safety determined by the system 10. In one embodiment of nerve detection, set forth by way of example only, a green display corresponds to a stimulation threshold range of 10 milliamps (mA) or greater, a yellow display denotes a stimulation threshold range of 5-9 mA, and a red display denotes a stimulation threshold range of 4 mA or below. FIG. 21 illustrates the detection function without EMG waveforms 116 and FIG. 22 illustrates the detection function with the EMG waveforms 116 displayed.

The surgical system 10 accomplishes neural pathology monitoring, preferably after conducting a neuromuscular pathway test, by electrically stimulating a retracted nerve root via one or more stimulation electrodes at the distal end of the nerve root retractor 76 while monitoring the EMG responses of the muscle group innervated by the particular nerve. The EMG responses provide a quantitative measure of the nerve depolarization caused by the electrical stimulus. Analysis of the EMG responses may then be used to assess the degree to which retraction of a nerve or neural structure affects the nerve function over time, as will be described with greater particularity below. One advantage of such monitoring, by way of example only, is that the conduction of the nerve may be monitored during the procedure to determine whether the neurophysiology and/or function of the nerve changes (for the better or worse) as the result of the particular surgical procedure. For example, it may be observed that the nerve conduction increases as the result of the operation, indicating that the previously inhibited nerve has been positively affected by the operation. The nerve root retractor 76 (FIG. 1) may comprise any number of suitable devices capable of maintaining contact with a nerve or nerve root. The nerve root retractor 76 may be dimensioned in any number of different fashions, including having a generally curved distal region (shown as a side view in FIG. 1 to illustrate the concave region where the nerve will be positioned while retracted), and of sufficient dimension (width and/or length) and rigidity to maintain the retracted nerve in a desired position during surgery. The nerve root retractor 76 may also be equipped with a stimulation handle 78 (similar to the stimulation handpiece 34 described above) having one or more buttons for selectively applying the electrical stimulation to the stimulation electrode(s) at the end of the nerve root retractor 76. In one embodiment, the nerve root retractor 76 is disposable and the stimulation handle 78 is reusable and autoclavable.

Figure 23:
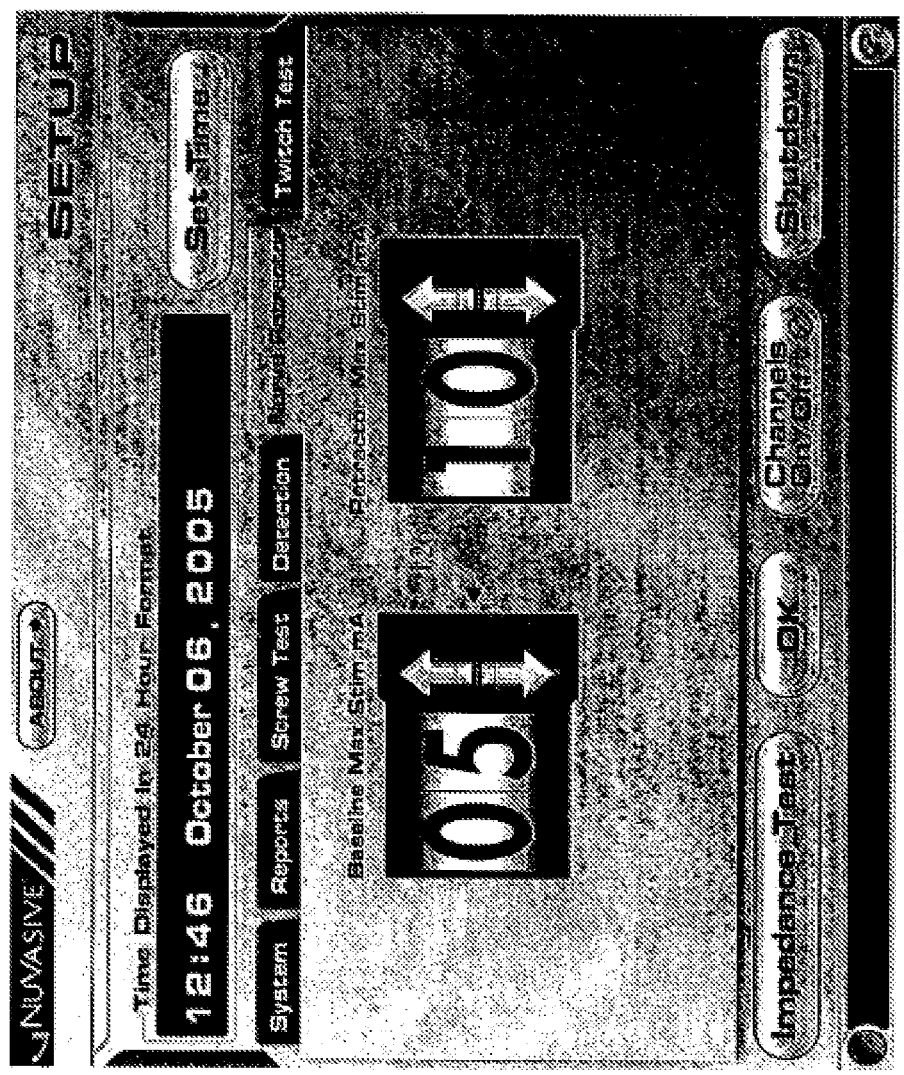
FIG. 23 is an exemplary screen display illustrating one embodiment of a Nerve Retractor (pathology) setup screen according to the present invention.
Figure 24:
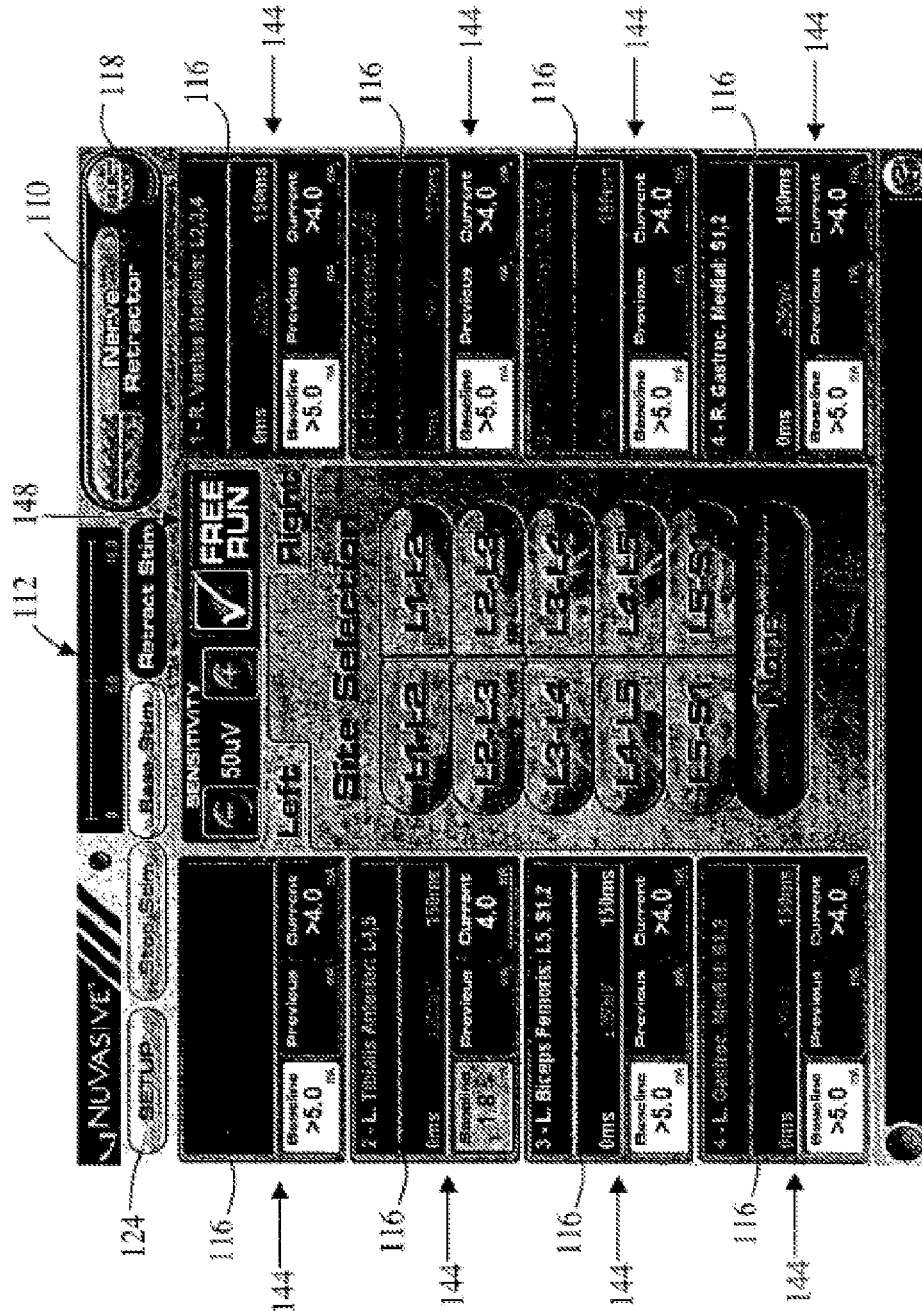
FIG. 24 is an exemplary screen displays illustrating one embodiment of the Nerve Retractor function according to the present invention.

In a preferred embodiment, nerve pathology is monitored via the Nerve Retractor function specifically by determining a baseline stimulation threshold with direct contact between the nerve retractor 76 and the nerve but prior to retraction. Subsequently, additional stimulation thresholds are determined during retraction and they are compared to the baseline threshold. Significant changes in the stimulation threshold may indicate potential trauma to the nerve caused by the retraction. The information regarding nerve pathology is conveyed to the surgeon via the nerve retractor screen display, shown by way of example only in FIG. 24. The function indicator 110 shows that Nerve Retractor is the active function and stimulation bar 112 graphically depicts the stimulation current level. A channel window 144 is provided for each EMG channel. Included in the channel window is information including the channel number, myotome name and associated spinal level, the EMG waveform 116, the baseline threshold, current detected threshold, and the previous detected threshold. Site selection buttons 146 allow the surgeon to quickly annotate a threshold response with the spinal level stimulated. The EMG sensitivity and Free-Run status are also displayed 148 on the screen. In the event the system 10 detects a significant difference between the baseline threshold and the current threshold on a particular channel, the associated channel window may preferably be highlighted to indicate the potential danger to the surgeon. The maximum allowable stimulation currents for both the baseline and retractor stimulations may be set or changed manually using the up and down control arrows 126 on the nerve retractor setup screen, shown by way of example only in FIG. 23. In addition the user may turn different channels on or off, set the date and time, conduct an impedance test to check the electrical connection between the EMG electrodes and the patient's skin, and shutdown the system 10, all from the same setup screen.

Figure 25:
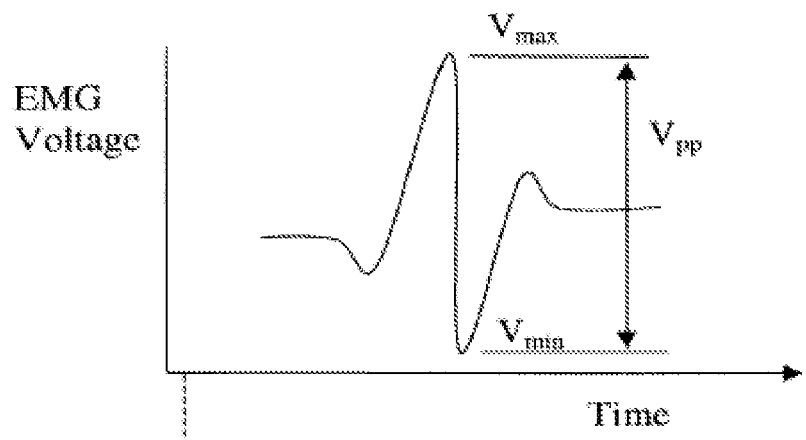
FIG. 25 is a graph illustrating a plot of the neuromuscular response (EMG) of a given myotome over time based on a current stimulation pulse (similar to that shown in FIG. 26) applied to a nerve bundle coupled to the given myotome.
Figure 26:
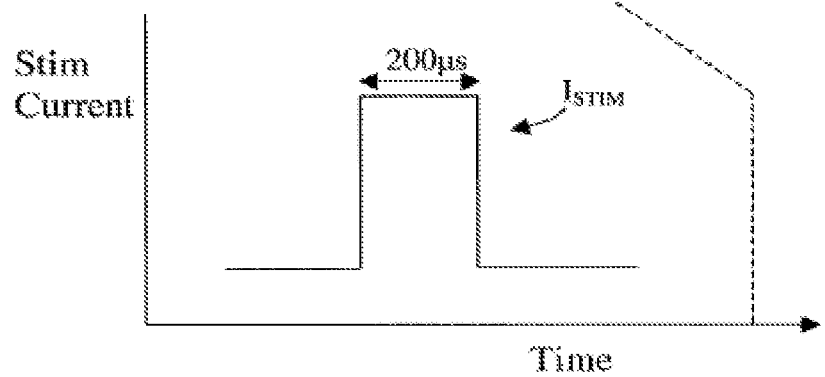
FIG. 26 is a graph illustrating a plot of a stimulation current pulse capable of producing a neuromuscular response (EMG) of the type shown in FIG. 25.

The nerve testing functions mentioned above (screw test, nerve proximity, nerve pathology) are based on assessing the evoked response of the various muscles myotomes monitored by the surgical system 10, preferably via the EMG electrodes 18. This is best shown in FIG. 25-26, wherein FIG. 25 illustrates the EMG of a monitored myotome to the stimulation current pulse shown in FIG. 26. The EMG response can be characterized by a peak-to-peak voltage of $V_{pp}=V_{max}-V_{min}$. The stimulation current may be coupled in any suitable fashion (i.e. AC or DC) and comprises monophasic pulses of 200 μs duration, with an amplitude and frequency that is controlled and adjusted by the software. For each nerve and myotome there is a characteristic delay from the stimulation current pulse to the EMG response (typically between 5 to 20 ms). To account for this, the frequency of the current pulses is set at a suitable level such as, in a preferred embodiment, 4 Hz to 10 Hz (and most preferably 4.5 Hz), so as to prevent stimulating the nerve before it has a chance to recover from depolarization.

Figure 27:
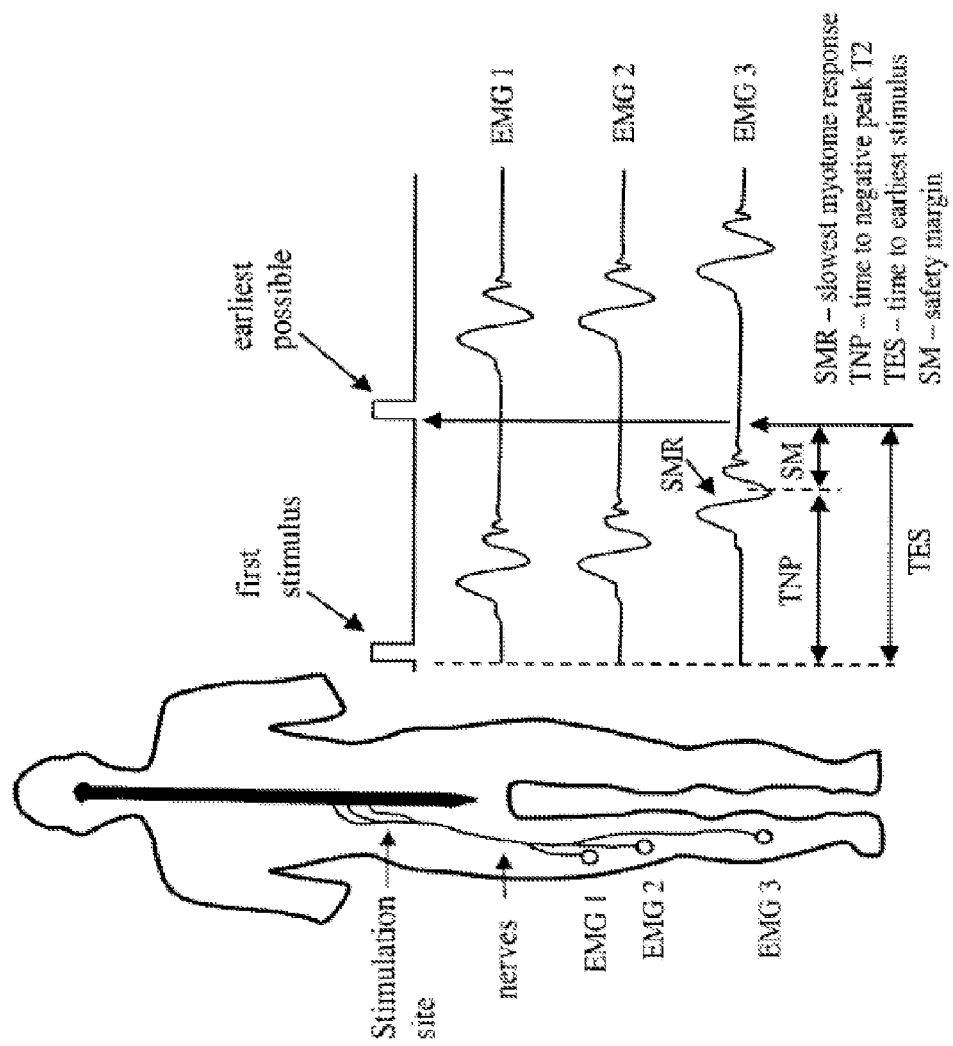
FIG. 27 is an illustration (graphical and schematic) of a method of automatically determining the maximum frequency ($F_{Max}$) of the stimulation current pulses according to one embodiment of the present invention.

FIG. 27 illustrates an alternate manner of setting the maximum stimulation frequency ($F_{max}$), to the extent it is desired to do so rather than simply selecting a fixed maximum stimulation frequency (such as 4.5 Hz) as described above. According to this embodiment, the maximum frequency of the stimulation pulses is automatically adjusted. After each stimulation, $F_{max}$ will be computed as: $F_{max}=1/(T2+T_{Safety\ Margin})$ for the largest value of T2 from each of the active EMG channels. In one embodiment, the Safety Margin is 5 ms, although it is contemplated that this could be varied according to any number of suitable durations. Before the specified number of stimulations, the stimulations will be performed at intervals of 100-120 ms during the bracketing state, intervals of 200-240 ms during the bisection state, and intervals of 400-480 ms during the monitoring state (bracketing, bisection and monitoring states are discussed in detail below). After the specified number of stimulations, the stimulations will be performed at the fastest interval practical (but no faster than $F_{max}$) during the bracketing state, the fastest interval practical (but no faster than $F_{max}/2$) during the bisection state, and the fastest interval practical (but no faster than $F_{max}/4$) during the monitoring state. The maximum frequency used until $F_{max}$ is calculated is preferably 10 Hz, although slower stimulation frequencies may be used during some acquisition algorithms. The value of $F_{max}$ used is periodically updated to ensure that it is still appropriate. For physiological reasons, the maximum frequency for stimulation will be set on a per-patient basis. Readings will be taken from all myotomes and the one with the slowest frequency (highest T2) will be recorded.

Figure 28:
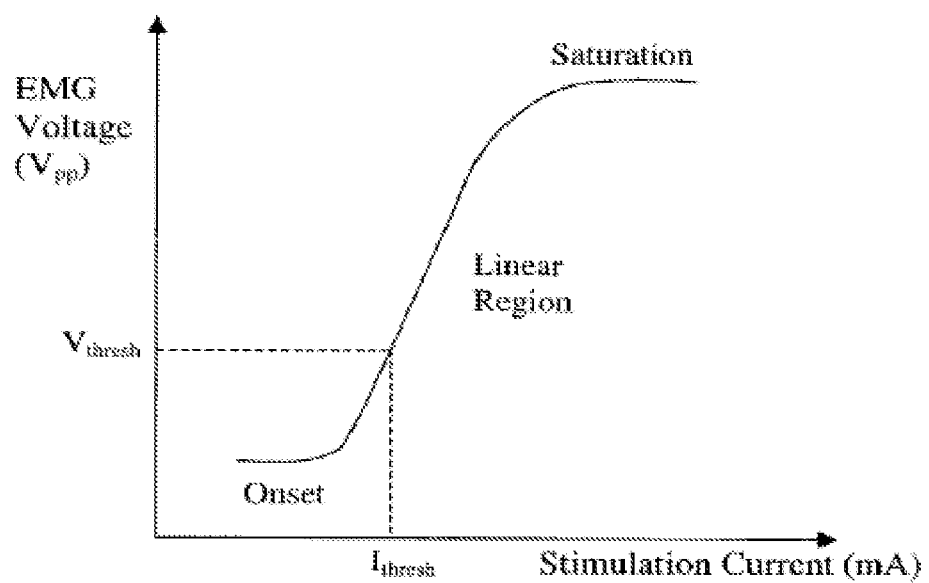
FIG. 28 is a graph illustrating a plot of peak-to-peak voltage (Vpp) for each given stimulation current level ($I_{Stim}$) forming a stimulation current pulse train according to the present invention (otherwise known as a "recruitment curve")

A basic premise behind the neurophysiology employed for nerve testing in the present invention is that each nerve has a characteristic threshold current level ($I_{Thresh}$) at which it will depolarize. Below this threshold, current stimulation will not evoke a significant EMG response ($V_{pp}$). Consequently, it is this premise that makes NMP testing a valuable step in nerve testing because $I_{thresh}$ may be significantly altered in the presence of high levels of NMB. Once the stimulation threshold ($I_{Thresh}$) is reached, the evoked response is reproducible and increases with increasing stimulation until saturation is reached as shown in FIG. 28. This is known as a "recruitment curve." In one embodiment, a significant EMG response is defined to have a $V_{pp}$ of approximately 100 uV. The lowest stimulation current that evokes this threshold voltage ($V_{Thresh}$) is called $I_{Thresh}$. $I_{thresh}$ decreases as the degree of electrical communication between a stimulation impulse and a nerve increases. Thus, monitoring $I_{thresh}$, can provide the surgeon with useful information. For example, obtaining a lower than expected $I_{thresh}$ when applying a stimulation impulse to the tip of a pedicle screw (or the interior of a pilot hole) may indicate electrical communication between the stimulation element and the nerve, such communication being indicative of a breach in the pedicle. Monitoring $I_{thresh}$ may also be employed to provide the surgeon with a relative indication of distance from the stimulation electrode to a nerve.

In order to obtain $I_{thresh}$ and take advantage of the useful information it provides, the peak-to-peak voltage ($V_{pp}$) of each EMG response corresponding a given stimulation current ($I_{Stim}$) must be identified. This may be complicated by the existence of stimulation and/or noise artifacts which may create an erroneous $V_{pp}$ measurement of the electrically evoked EMG response. To overcome this challenge, the surgical system 10 of the present invention may employ any number of suitable artifact rejection techniques such as those shown and described in full in the above referenced PCT App. Ser. No. PCT/US2004/025550, entitled "System and Methods for Performing Dynamic Pedicle Integrity Assessments," filed on Aug. 5, 2004, the contents of which are hereby incorporated by reference into this disclosure as if set forth herein in their entireties.

Having measured each $V_{pp}$ EMG response, the $V_{pp}$ information is analyzed relative to the stimulation current in order to determine a relationship between the nerve and the given stimulation element transmitting the stimulation current. More specifically, the present invention determines these relationships (between nerve and the stimulation element) by identifying the minimum stimulation current ($I_{thresh}$) capable of resulting in a predetermined $V_{pp}$ EMG response. According to the present invention, the determination of $I_{Thresh}$ may be accomplished via any of a variety of suitable algorithms or techniques.

FIGS. 29A-29D illustrate, by way of example only, a threshold-hunting algorithm that employs a series of monopolar electrical stimulations to determine the stimulation current threshold $I_{thresh}$ for each EMG channel in range. The nerve is stimulated using current pulses with amplitude of $I_{stim}$. The muscle groups respond with an evoked potential that has a peak-to-peak voltage of $V_{pp}$. The object of this algorithm is to quickly find $I_{Thresh}$, which once again, is the minimum $I_{stim}$ that results in a $V_{pp}$ that is greater than a known threshold voltage $V_{thresh}$. The value of $I_{stim}$ is adjusted by a bracketing method as follows. The first bracket is 0.2 mA and 0.3 mA. If the $V_{pp}$ corresponding to both of these stimulation currents is lower than $V_{thresh}$, then the bracket size is doubled to 0.2 mA and 0.4 mA. This exponential doubling of the bracket size continues until the upper end of the bracket results in a $V_{pp}$ that is above $V_{thresh}$. The size of the brackets is then reduced by a bisection method. A current stimulation value at the midpoint of the bracket is used and if this results in a $V_{pp}$ that is above $V_{thresh}$, then the lower half becomes the new bracket. Likewise, if the midpoint $V_{pp}$ is below $V_{thresh}$ then the upper half becomes the new bracket. This bisection method is used until the bracket size has been reduced to Ires mA. $I_{Thresh}$ is the value of $I_{stim}$ that is the higher end of the bracket.

The threshold hunting will support three states: bracketing, bisection, and monitoring. A stimulation current bracket is a range of stimulation currents that bracket the stimulation current threshold $I_{Thresh}$. The upper and/or lower boundaries of a bracket may be indeterminate. The width of a bracket is the upper boundary value minus the lower boundary value. If the stimulation current threshold $I_{Thresh}$ of a channel exceeds the maximum stimulation current, that threshold is considered out-of-range. During the bracketing state, threshold hunting will employ the method below to select stimulation currents and identify stimulation current brackets for each EMG channel in range.

The method for finding the minimum stimulation current uses the methods of bracketing and bisection. The "root" is identified for a function that has the value −1 for stimulation currents that do not evoke adequate response; the function has the value +1 for stimulation currents that evoke a response. The root occurs when the function jumps from −1 to +1 as stimulation current is increased: the function never has the value of precisely zero. The root will not be known precisely, but only with some level of accuracy. The root is found by identifying a range that must contain the root. The upper bound of this range is the lowest stimulation current $I_{Thresh}$ where the function returns the value +1 (i.e. the minimum stimulation current that evokes response).

Figure 29A:
FIGS. 29A-29D are graphs illustrating a rapid current threshold-hunting algorithm according to one embodiment of the present invention.
Figure 29B:
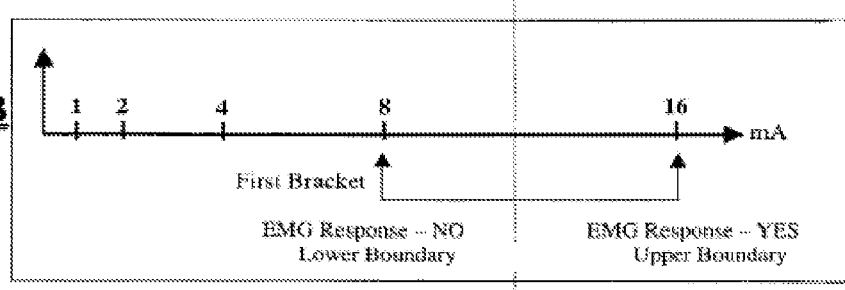
Figure 29C:
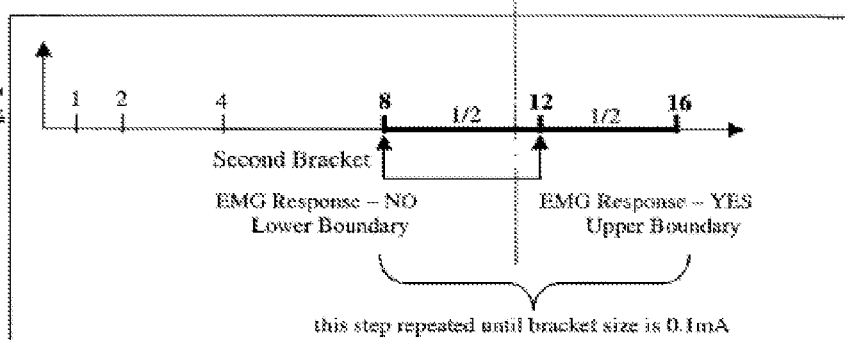
Figure 29D:
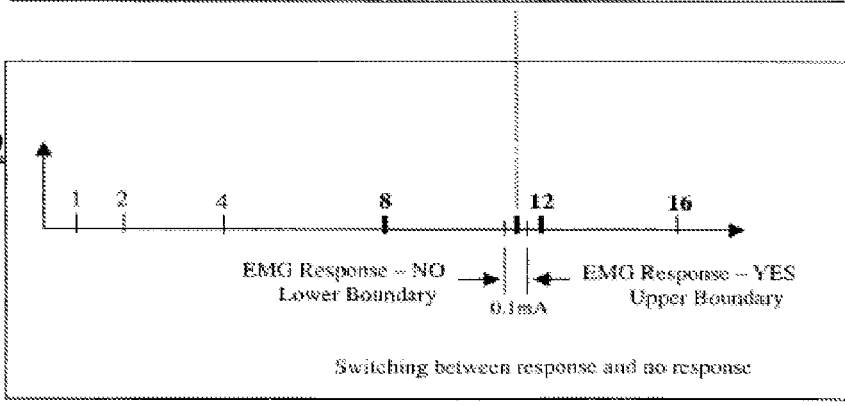

Both the screw test function and the proximity function, as well as the optional NMP baseline setting method utilizing $I_{thresh}$ (described above), begin by adjusting the stimulation current from the surgical accessory until the root is bracketed (FIG. 29B). The initial bracketing range may be provided in any number of suitable ranges. In one embodiment, the initial bracketing range is 0.2 to 0.3 mA. If the upper stimulation current does not evoke a response, the upper end of the range should be increased. The range scale factor is 2. The stimulation current should never be increased by more than 10 mA in one iteration. The stimulation current should never exceed the programmed maximum stimulation current. For each stimulation, the algorithm will examine the response of each active channel to determine whether it falls within that bracket. Once the stimulation current threshold of each channel has been bracketed, the algorithm transitions to the bisection state.

During the bisection state (FIG. 29C), threshold hunting will employ the method described below to select stimulation currents and narrow the bracket to a width of 0.1 mA for each EMG channel with an in-range threshold. After the minimum stimulation current has been bracketed (FIG. 29C), the range containing the root is refined until the root is known with a specified accuracy. The bisection method is used to refine the range containing the root. In one embodiment, the root should be found to a precision of 0.1 mA. During the bisection method, the stimulation current at the midpoint of the bracket is used. If the stimulation evokes a response, the bracket shrinks to the lower half of the previous range. If the stimulation fails to evoke a response, the bracket shrinks to the upper half of the previous range. The algorithm is locked on the electrode position when the response threshold is bracketed by stimulation currents separated by 0.1 mA. The process is repeated for each of the active channels until all thresholds are precisely known. At that time, the algorithm enters the monitoring state.

During the monitoring state (FIG. 29D), threshold hunting will employ the method described below to select stimulation currents and identify whether stimulation current thresholds are changing. In the monitoring state, the stimulation current level is decremented or incremented by 0.1 mA, depending on the response of a specific channel. If the threshold has not changed then the lower end of the bracket should not evoke a response, while the upper end of the bracket should. If either of these conditions fail, the bracket is adjusted accordingly. The process is repeated for each of the active channels to continue to assure that each threshold is bracketed. If stimulations fail to evoke the expected response three times in a row, then the algorithm transitions back to the bracketing state in order to reestablish the bracket.

Figure 30:
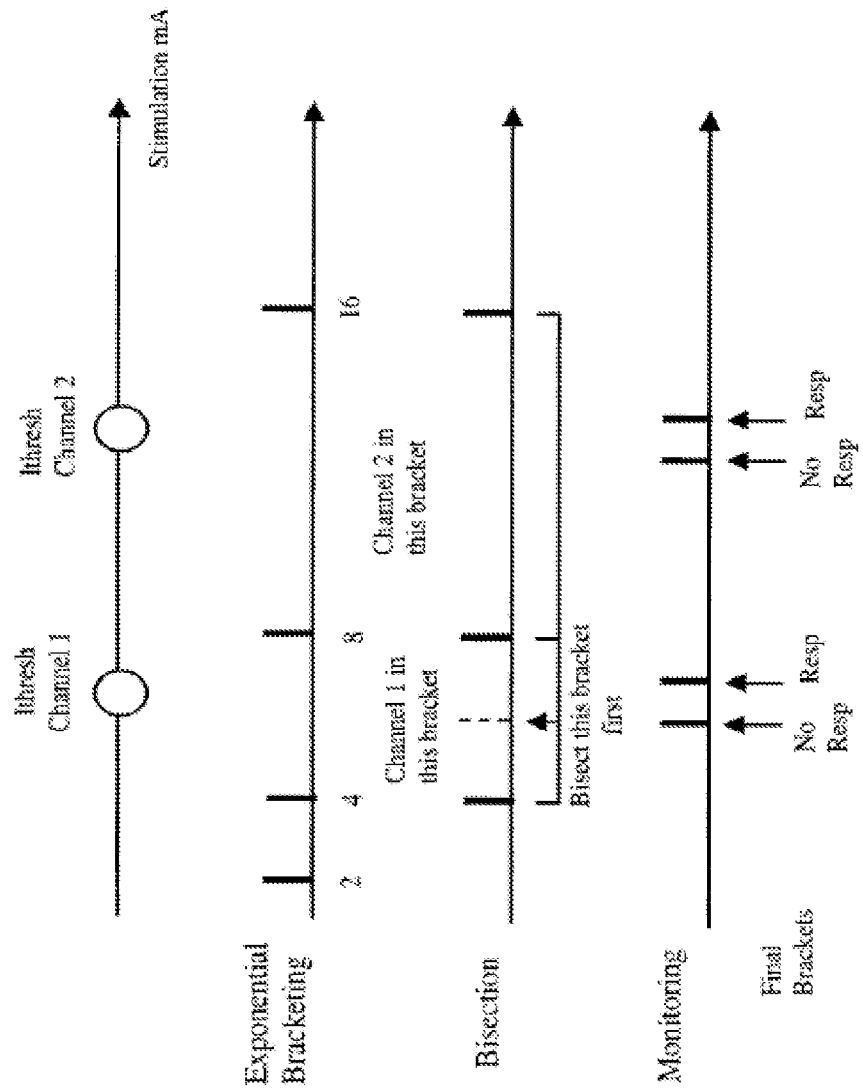
FIG. 30 is a series of graphs illustrating a multi-channel rapid current threshold-hunting algorithm according to one embodiment of the present invention.

When it is necessary to determine the stimulation current thresholds ($I_{thresh}$) for more than one channel, they may be obtained by time-multiplexing the threshold-hunting algorithm as shown in FIG. 30. During the bracketing state, the algorithm will start with a stimulation current bracket of 0.2 mA and increase the size of the bracket exponentially. With each bracket, the algorithm will measure the $V_{pp}$ of all channels to determine which bracket they fall into. After this first pass, the algorithm will know which exponential bracket contains the $I_{thresh}$ for each channel. Next, during the bisection state, the algorithm will start with the lowest exponential bracket that contains an $I_{thresh}$ and bisect it until $I_{thresh}$ is found within 0.1 mA. If there are more than one $I_{thresh}$ within an exponential bracket, they will be separated out during the bisection process, and the one with the lowest value will be found first. During the monitoring state, the algorithm will monitor the upper and lower boundaries of the brackets for each $I_{thresh}$, starting with the lowest. If the $I_{thresh}$ for one or more channels is not found in it's bracket, then the algorithm goes back to the bracketing state to re-establish the bracket for those channels.

Insertion and advancement of the access instruments 62-66, 70 should be performed at a rate sufficiently slow to allow the surgical system 10 to provide real-time indication of the presence of nerves that may lie in the path of the tip. To facilitate this, the threshold current $I_{Thresh}$ may be displayed such that it will indicate when the computation is finished and the data is accurate. For example, when the detection information is up to date and the instrument such that it is now ready to be advanced by the surgeon, it is contemplated to have the color display show up as saturated to communicate this fact to the surgeon. During advancement of the instrument, if a channel's color range changes from green to yellow, advancement should proceed more slowly, with careful observation of the detection level. If the channel color stays yellow or turns green after further advancement, it is a possible indication that the instrument tip has passed, and is moving farther away from the nerve. If after further advancement, however, the channel color turns red, then it is a possible indication that the instrument tip has moved closer to a nerve. At this point the display will show the value of the stimulation current threshold in mA. Further advancement should be attempted only with extreme caution, while observing the threshold values, and only if the surgeon deems it safe. If the surgeon decides to advance the instrument tip further, an increase in threshold value (e.g. from 3 mA to 4 mA) may indicate the instrument tip has safely passed the nerve. It may also be an indication that the instrument tip has encountered and is compressing the nerve. The latter may be detected by listening for sporadic outbursts, or "pops", of nerve activity on a free running EMG audio output (as mentioned below). If, upon further advancement of the instrument, the alarm level decreases (e.g., from 4 mA to 3 mA), then it is very likely that the instrument tip is extremely close to the spinal nerve, and to avoid neural damage, extreme caution should be exercised during further manipulation of the instrument. Under such circumstances, the decision to withdraw, reposition, or otherwise maneuver the instrument is at the sole discretion of the clinician based upon available information and experience.

Further radiographic imaging may be deemed appropriate to establish the best course of action.

Figure 31:
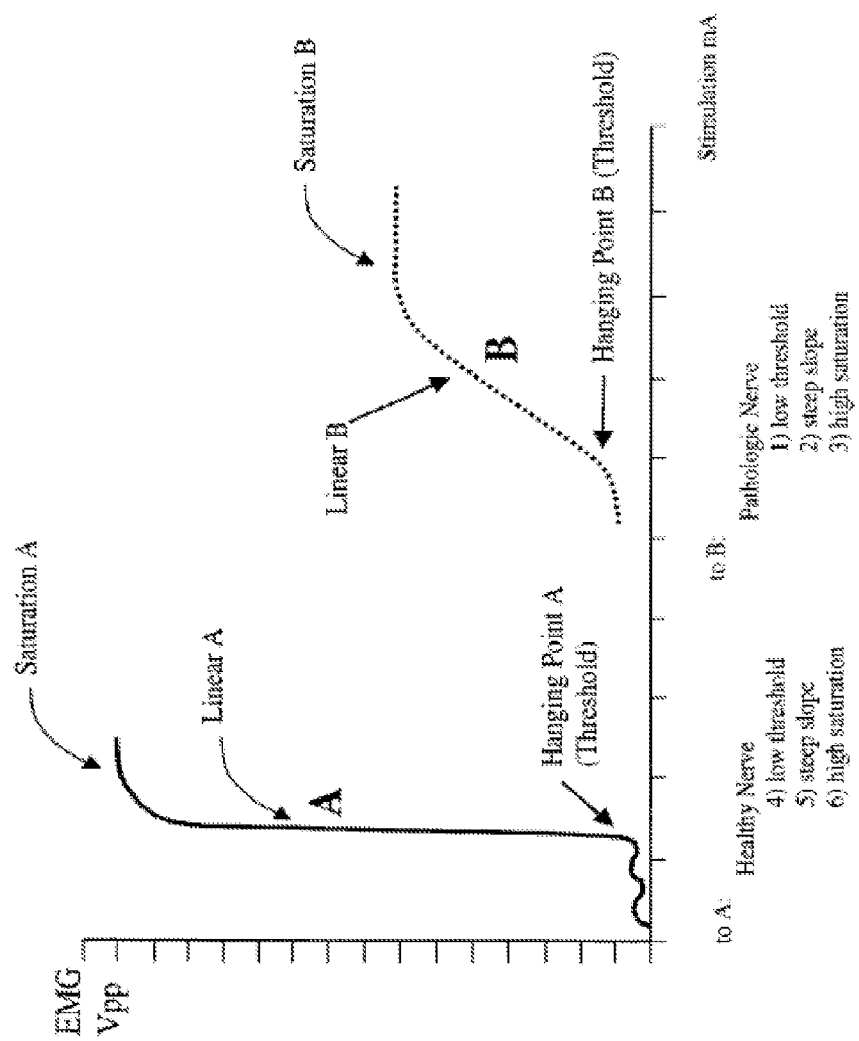
FIG. 31 is a graph illustrating recruitment curves for a generally healthy nerve (denoted "A") and a generally unhealthy nerve (denoted "B") according to the nerve pathology determination method of the present invention.

As noted above, the surgical system 10 accomplishes neural pathology monitoring by electrically stimulating a retracted nerve root via one or more stimulation electrodes at the distal end of the nerve root retractor 76 while monitoring the EMG responses of the muscle group innervated by the particular nerve. FIG. 31 shows the differences between a healthy nerve (A) and a pathologic or unhealthy nerve (B). The inventors have found through experimentation that information regarding nerve pathology (or "health" of "status") can be extracted from the recruitment curves generated according to the present invention (see, e.g., discussion accompanying FIGS. 25-28). In particular, it has been found that a healthy nerve or nerve bundle will produce a recruitment curve having a generally low threshold or "hanging point" (in terms of both the y-axis or $V_{pp}$ value and the x-axis or $I_{Stim}$ value), a linear region having a relatively steep slope, and a relatively high saturation region (similar to those shown on recruitment curve "A" in FIG. 31). On the contrary, a nerve or nerve bundle that is unhealthy or whose function is otherwise compromised or impaired (such as being impinged by spinal structures or by prolonged retraction) will produce recruitment curve having a generally higher threshold (again, in terms of both the y-axis or $V_{pp}$ value and the x-axis or $I_{Stim}$ value), a linear region of reduced slope, and a relatively low saturation region (similar to those shown on recruitment curve "B" in FIG. 31). By recognizing these characteristics, one can monitor nerve root being retracted during a procedure to determine if its pathology or health is affected (i.e. negatively) by such retraction. Moreover, one can monitor a nerve root that has already been deemed pathologic or unhealthy before the procedure (such as may be caused by being impinged by bony structures or a bulging annulus) to determine if its pathology or health is affected (i.e. positively) by the procedure.

In addition to the directed nerve testing functions described above, the surgical system 10 also preferably performs passive monitoring via free run EMG conducted continuously from the EMG electrodes 18 when other functions are not active. In doing so, the operating user may be alerted to any nerve activity occurring unexpectedly. An audio pick-up (not shown) may also be provided as an optional feature according to the present invention. In some cases, when a nerve is stretched or compressed, it will emit a burst or train of spontaneous nerve activity. The audio pick-up is capable of transmitting sounds representative of such activity such that the surgeon can monitor this response on audio to help him determine if there has been stress to the nerve.

Figure 32A:
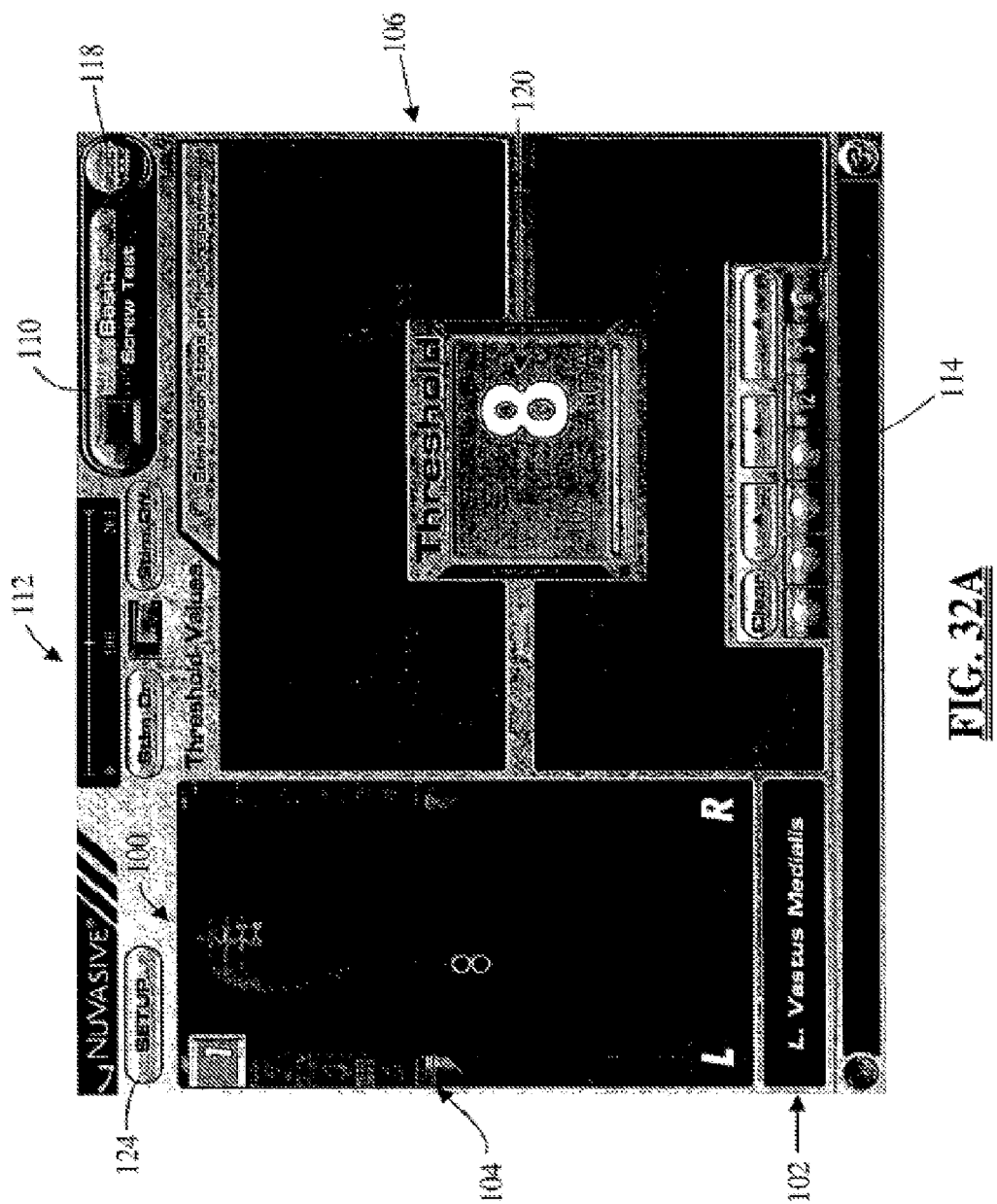
FIGS. 32A-32E are exemplary screen displays illustrating one method of annotating selected stimulation results according to one embodiment of the present invention.
Figure 32B:
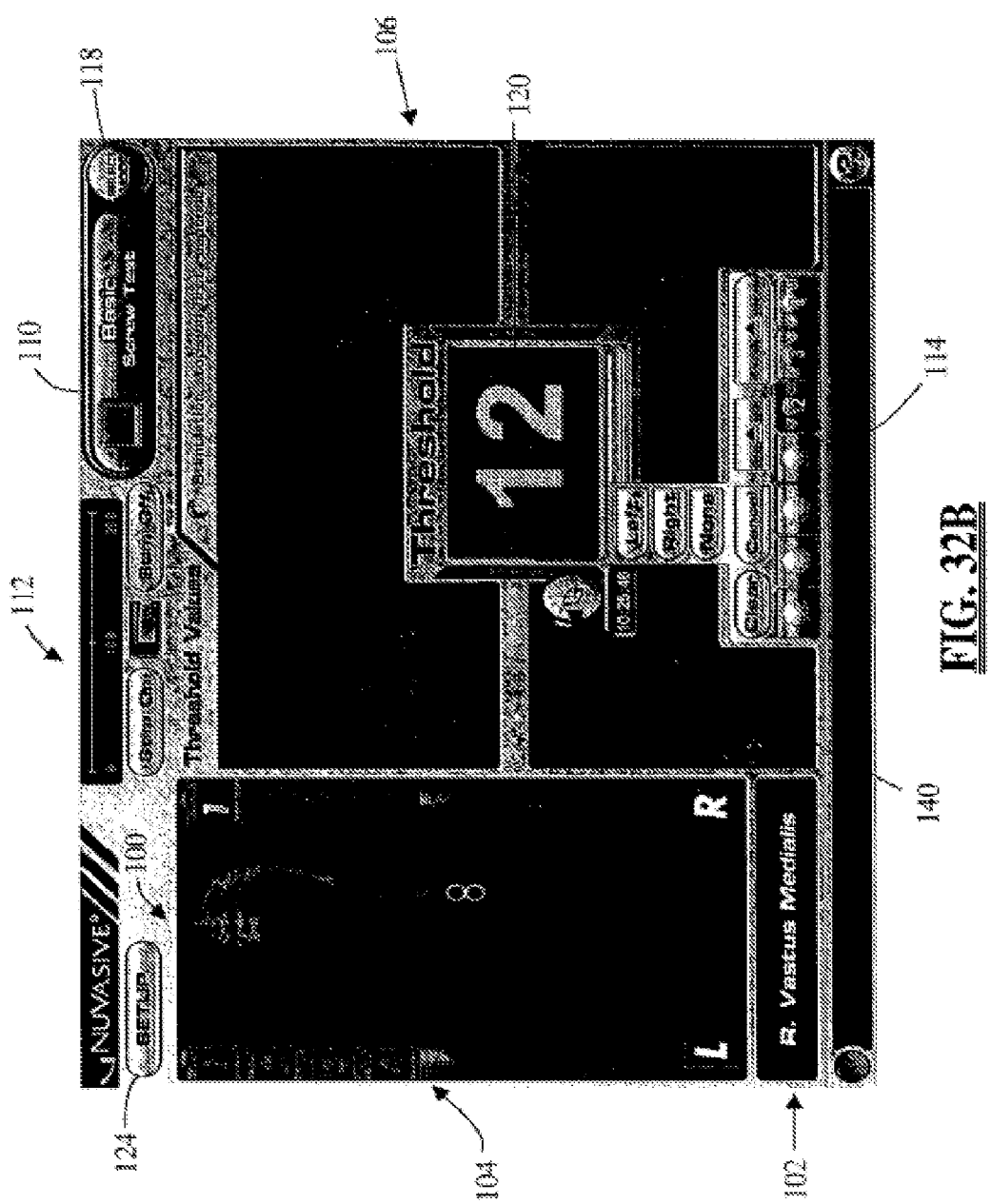
Figure 32C:
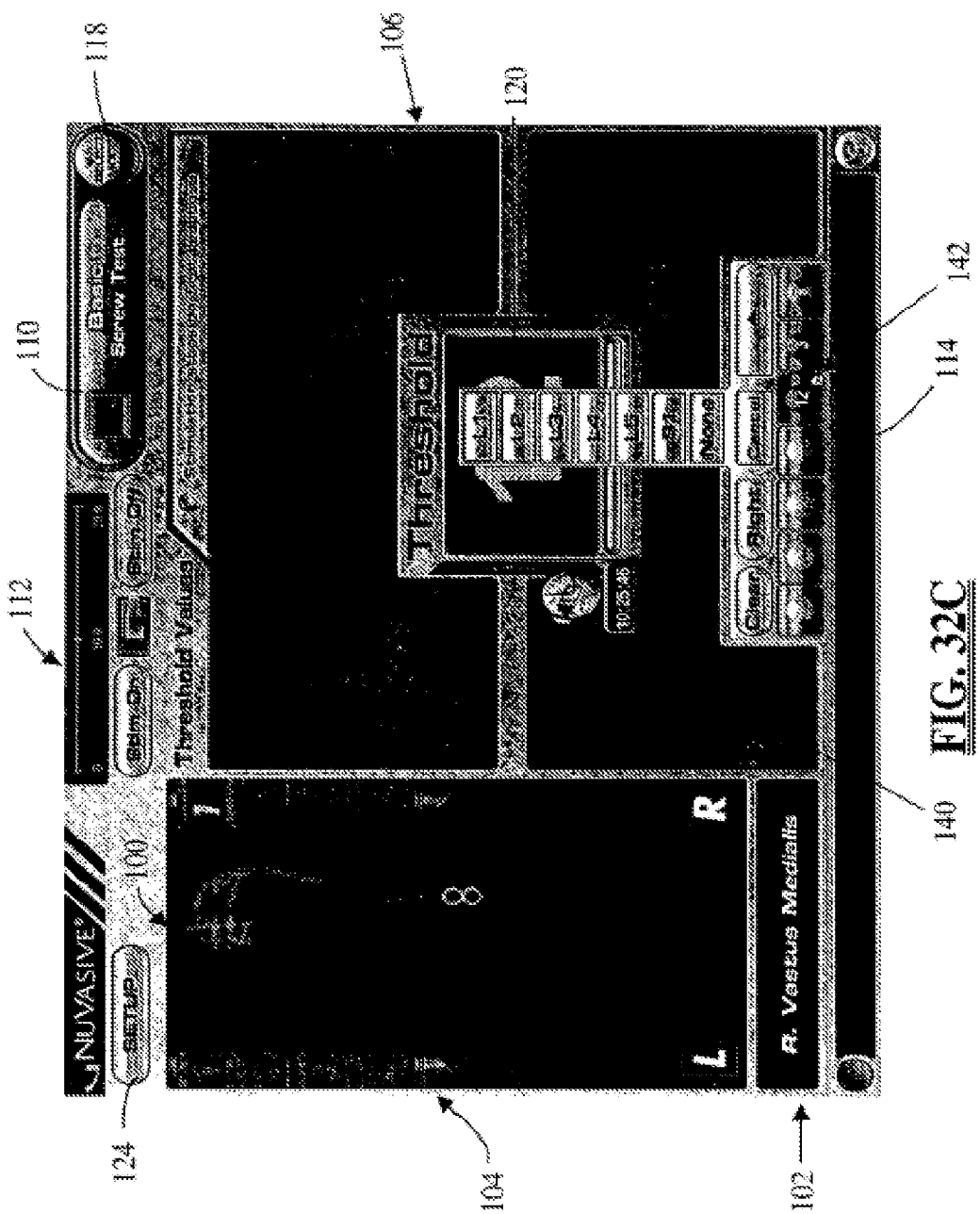
Figure 32D:
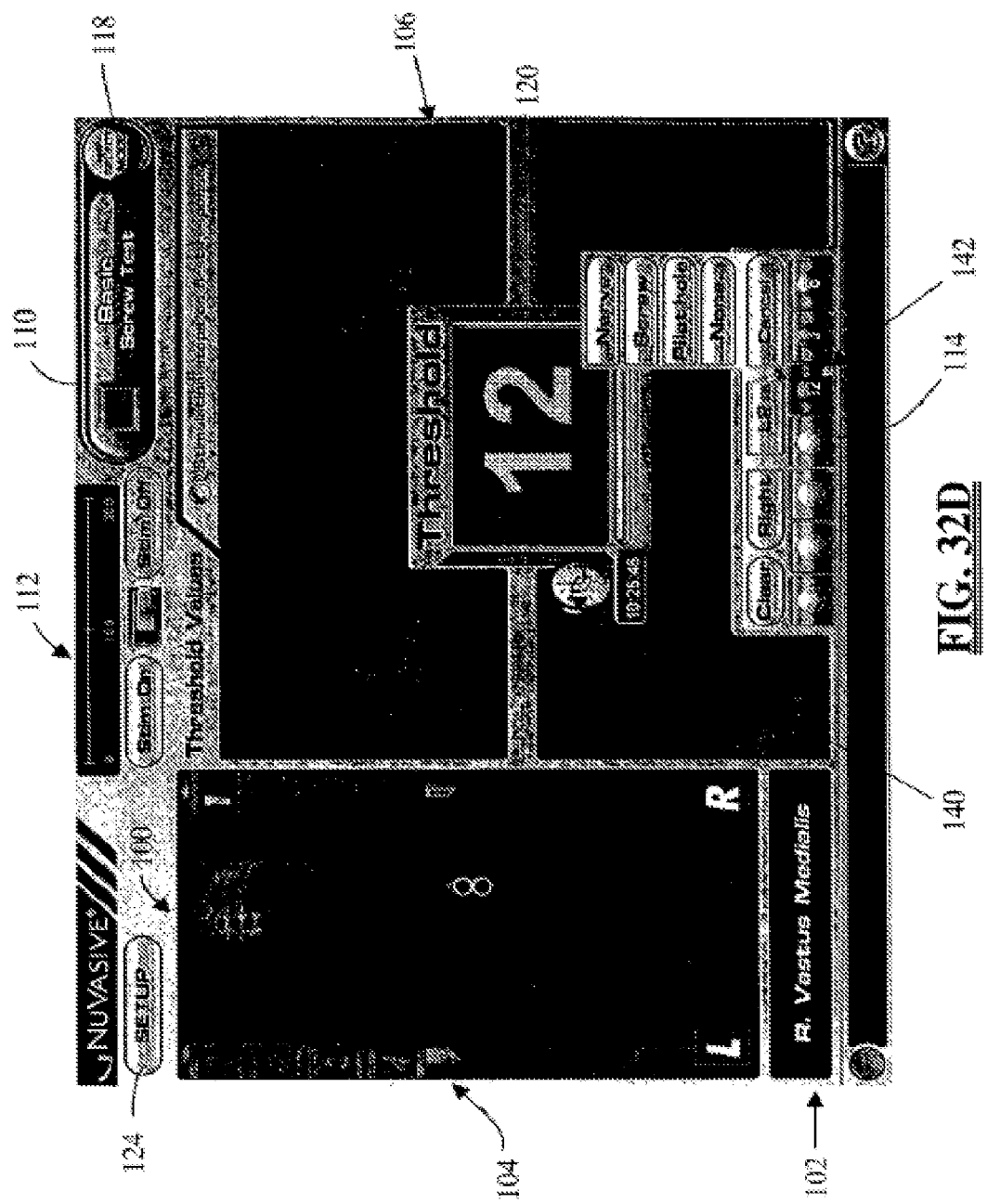
Figure 32E:
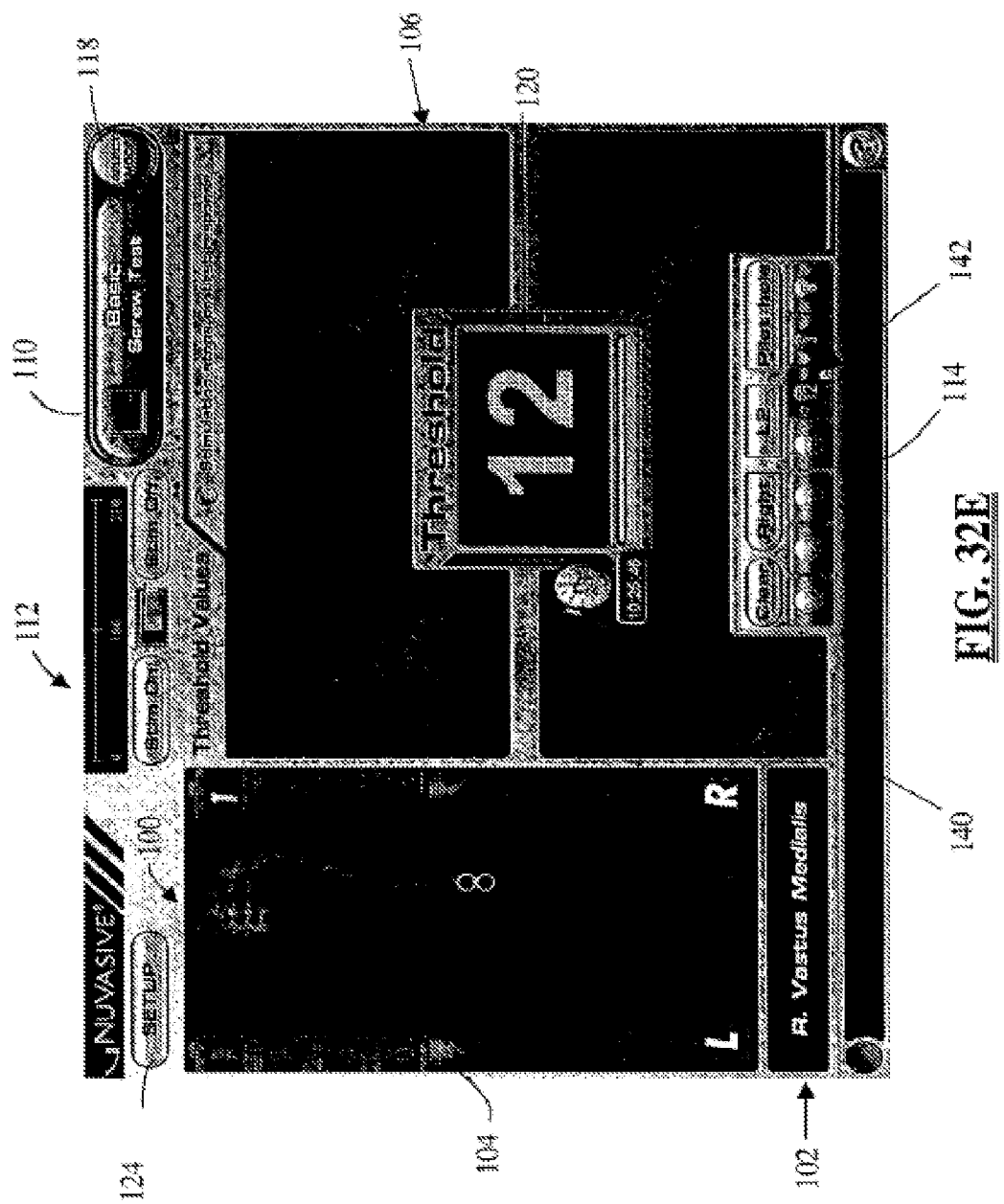

To facilitate record keeping, results from the various functions described above are preferably saved by the system 10 throughout the surgical procedure and a report may be generated containing all of the stimulation results. To enhance the clarity and usefulness of the reported data the surgical system 10 provides a method for quickly and easily annotating each stimulation result with additional relevant information including, but not necessarily limited to, the side and level where the stimulation occurred as well as the structure stimulated (e.g. nerve, screw, or pilot hole). FIGS. 32A-32E illustrate one method of annotating stimulation responses according to a preferred embodiment of the present invention. With reference to FIG. 32A a sequence bar 114 may be included on the various result screens described above. The sequence bar may preferably display up to the last seven stimulation results in chronological order beginning with the most recent result. Annotations may be added to any or all of the results by selecting the desired result using the GUI display 26. The selected result will appear on the screen along with a time indicator 140 showing the precise time at which the result was obtained. Again using the GUI display 26 at least one of the side, spinal level, and structure stimulated may be selected, as shown in FIGS. 32B, 32C, and 32C, respectively. The annotated data is saved along with the stimulation result 120 and may be reproduced in a subsequent surgical report. Annotated results may preferably be demarcated with a suitable icon 142 representing that it includes annotated information, as shown in FIG. 32E. It should be understood that although the annotation feature is demonstrated with respect to the screw test function, stimulation results for all of the functions described may be annotated using this method.

Figure 33:
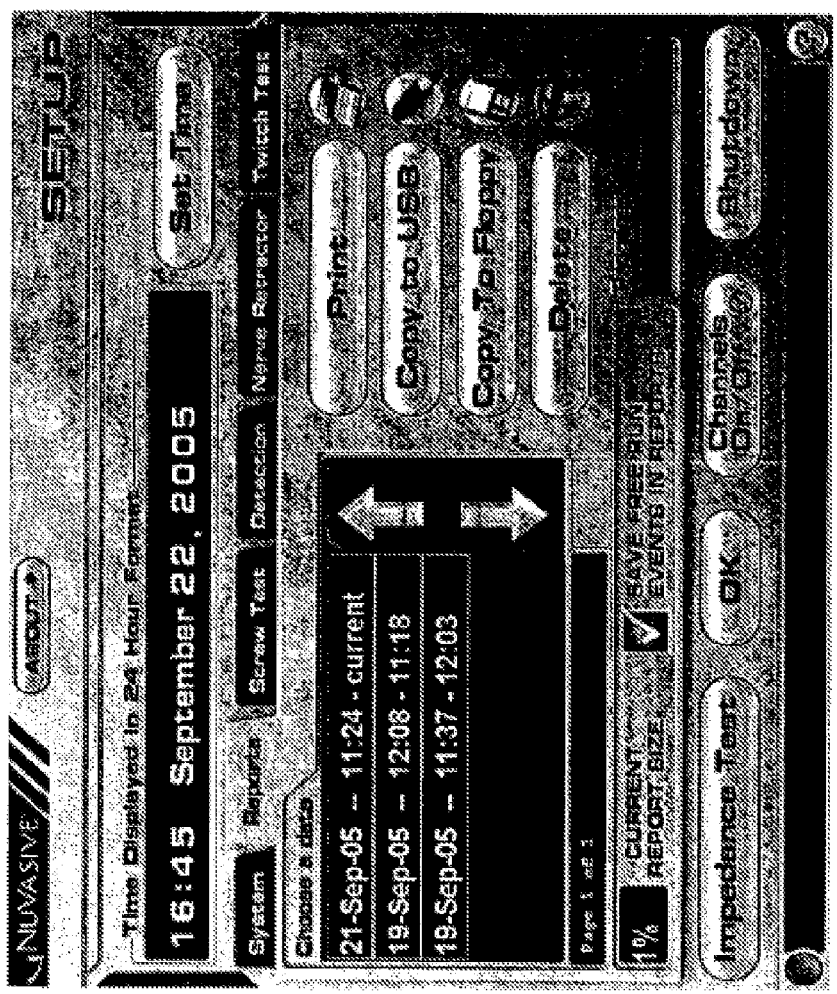
FIG. 33 is an exemplary screen display illustrating a method of generating a surgical report according to one embodiment of the present invention.
Figure 34:
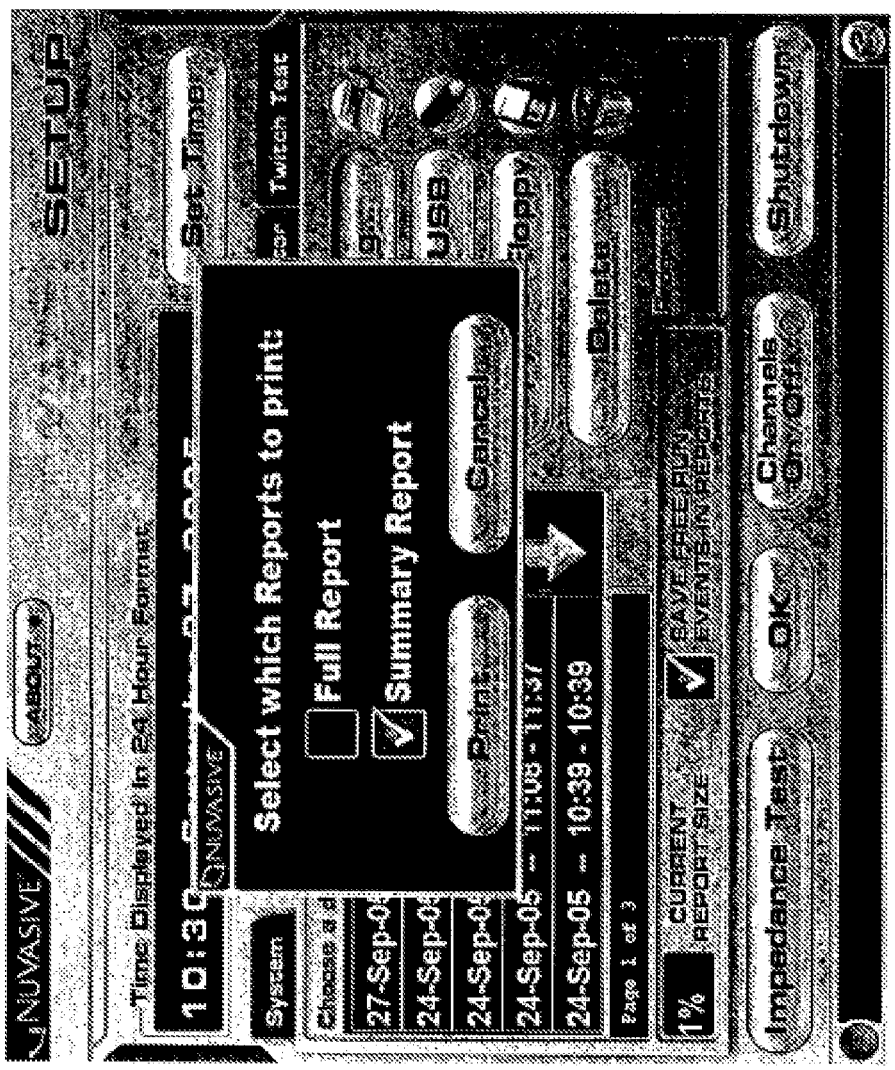
FIG. 34 is an exemplary screen display illustrating a method of selecting between a full surgical report and/or a summary surgical report according to one embodiment of the present invention.
Figure 35C:
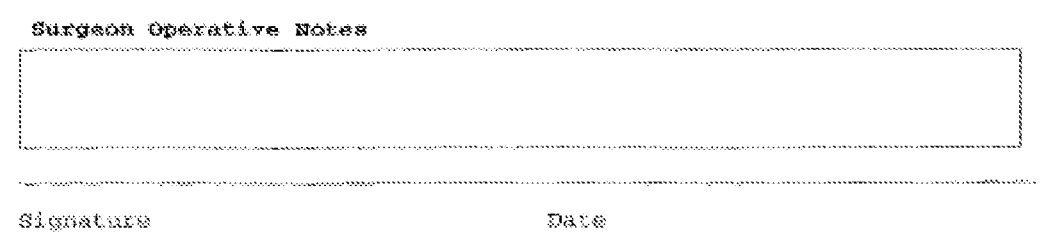
Figure 36A:
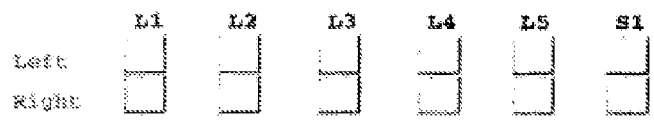

With reference to FIG. 33, the stimulation results, including annotations, may be compiled in a surgical report chronicling all nerve monitoring functions conducted during the procedure. In one embodiment, the report may be printed immediately from one or more printers located in the operating room or copied to any of a variety of memory devices known in the prior art, such as, by way of example only, a floppy disk, USB memory stick and/or transferred via infrared transmission technology to a handheld device such as a personal digital assistant (PDA). The system 10 may generate either a full report or a summary report depending the particular needs of the user, who may select one or both using the GUI screen display 26, as illustrated in FIG. 34. FIGS. 35A-35C are an exemplary representation of a summary report generated by system 10. The summary report includes space for patient, physician, and procedural information and surgeon operative notes along with the stimulation results. The stimulation results, including any annotated data, are preferably displayed in chronological order for each function. FIGS. 36A-36E are an exemplary representation of a full report generated by the system 10. The full report also includes space for patient and physician information and surgeon operative notes. The full stimulation results are displayed in chronological order regardless of the particular function.

The control unit 12 is configured to monitor the system status throughout its use. In the event the control unit 12 detects an aberration, an error log is created in which the details of the error are described and stored to assist in later troubleshooting and system correction. To service the system 10, the error logs may be accessed directly from the control unit 12 hardware and software. In addition, error logs may be downloaded onto any of a number of suitable media to facilitate data transfer between remote locations. By way of example only, the error logs may be downloaded to a USB memory device, floppy disk, CD, or DVD. By way of further example, the error logs may be downloaded onto a network and transmitted to remote locations via the Internet or other data transfer systems.

The surgeon-directed surgical system 10 of the present invention overcomes the drawbacks of the prior art and answers the previously unmet need in the prior art. The surgical system 10 boasts a number of techniques for performing neuromuscular pathway testing prior to nerve testing, such as pedicle integrity testing, nerve detection, and nerve pathology assessment, which advantageously minimizes the likelihood that the surgeon will obtain false positive assessments when performing such nerve testing procedures. Moreover, the surgical system 10 is capable of being controlled and interpreted by a surgeon without the assistance of a neurophysiologist (hence the term "surgeon-directed"). The complex task of EMG analysis is performed by the reliable and objective processing techniques of the present invention, which eliminates or at least reduces the potential for human error that is present with neurophysiologists. The surgeon-directed system 10 is quickly conveys the information in a straightforward and easy to understand (yet meaningful) manner, and does so under the command of the surgeon based on their immediate need (saving valuable surgery time). It also reduces the challenges involved in scheduling a neurophysiologist to assist with the surgery, as well as avoids the issue of making a patient wait (in pain) while the schedules of the surgeon and neurophysiologist coincide. Finally, the surgeon-directed system 10 combines the functional capability to perform nerve monitoring functions and the ability to ensure the safety and accuracy of those functions by assessing the neuromuscular pathway together in one easy to use, surgeon-directed system.

The surgical system 10 and related methods have been described above according to one embodiment of the present invention. It will be readily appreciated that various modifications may be undertaken, or certain steps or algorithms omitted or substituted, without departing from the scope of the present invention. By way of example only, certain of these alternate embodiments or methods will be described below. Moreover, although described with reference to the surgical system 10, it will particularly be appreciated as within the scope of the invention to perform the neuromuscular pathway test described herein with any number of different neurophysiology based testing systems.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the specified scope.

What is claimed is:

1. A surgical system for performing nerve testing during at least a portion of a surgical procedure, comprising:
   an accessory configured to transmit a stimulation signal to a nerve forming part of a neuromuscular pathway including a muscle myotome associated with the nerve;
   a sensor configured to detect evoked responses from the muscle myotome; and
   a control unit coupled to the accessory and the sensor, the control unit being operable to (a) transmit via an accessory a stimulation signal to a nerve forming part of the neuromuscular pathway including a muscle associated with the nerve, (b) monitor the evoked responses from a sensor associated with the muscle, (c) assess the neuromuscular pathway by identifying a relationship between the magnitude of at least two evoked responses, wherein the relationship provides an indication as to a level of a neuromuscular blockade within a patient's body prior to or during said nerve testing, and further wherein said nerve testing includes at least one of static pedicle integrity testing, dynamic pedicle integrity testing, nerve detection during surgical access, and nerve root retraction.

2. The surgical system of claim 1, wherein the relationship identified is the ratio between the magnitude of a first evoked response and a second evoked response.

3. The surgical system of claim 1, wherein the relationship identified is at least one of the presence and absence of the second evoked response.

4. The surgical system of claim 2, wherein the sensor is configured to detect an EMG voltage output of the muscle myotome and the control unit determines the magnitude of said EMG voltage output to characterize the evoked response.

5. The surgical system of claim 4, wherein the magnitude of the voltage output is characterized by a peak-to-peak amplitude.

6. The surgical system of claim 4, wherein the relationship identified is the ratio of the amplitude of the second evoked response versus the amplitude of the first evoked response.

7. The surgical system of claim 4, wherein the stimulation signal comprises four electric current pulses of equal magnitude and the relationship is the amplitude ratio of a fourth evoked response versus the amplitude of a first response.

8. The surgical system of claim 1, wherein the system assesses the neuromuscular pathway prior to a nerve testing during at least one of cervical, thoracic and lumbar spine surgery.

9. The surgical system of claim 1, wherein the system assesses the neuromuscular pathway by applying the stimulation signal at least one of on or near the nerve.

10. The surgical system of claim 1, wherein the system assesses the neuromuscular pathway by applying the stimulation signal to electrodes adapted to be placed over a peripheral nerve.

11. The surgical system of claim 1, wherein the stimulation signal includes at least two current pulses, each having a pulse duration and a delivery frequency.

12. The surgical system of claim 11, wherein the pulse duration is the range from 100 to 500 microseconds, and further wherein the delivery frequency of each pulse is in the range from 0.5 Hz to 5 Hz.

13. The surgical system of claim 11, wherein the amplitude of the current pulses is determined by assessing the threshold current required to obtain an evoked response.

14. The surgical system of claim 1, wherein the system assesses the neuromuscular pathway via an assessment that includes establishing a baseline current prior to the administration of a neuromuscular blocking agent.

15. The surgical system of claim 11, wherein the stimulation signal includes four current pulses.

16. The surgical system of claim 1, wherein the control unit is further configured to display at least one of alpha-numeric or graphical information regarding at least one of the stimulation signal, the neuromuscular responses, and the status of the neuromuscular pathway.

17. The surgical system of claim 1, wherein the sensor is configured to detect changes in pressure and the magnitude of the evoke responses is characterized by the measured pressure change.

18. The surgical system of claim 1, wherein the stimulation signal comprises four electrical current pulses of equal amplitude resulting in four corresponding evoked responses and the relationship identified is the ratio of the peak-to-peak amplitude of the fourth evoked response relative to the peak-to-peak amplitude of the first evoked response.

19. The surgical system of claim 1, wherein the stimulation signal comprises one electrical current pulse and the control unit calculates the ratio of the peak-to-peak amplitude of a first evoked response relative peak-to-peak amplitude of a predetermined baseline response.

20. The surgical system of claim 18, wherein the control unit is further configured to display at least one of a numerical value representing the amplitude ratio and a bar graph representing the relative amplitude for all four evoked responses.

* * * * *